(12) United States Patent
Foidart et al.

(10) Patent No.: US 9,238,035 B2
(45) Date of Patent: Jan. 19, 2016

(54) ESTROGENIC COMPONENTS FOR USE IN THE TREATMENT OF NEUROLOGICAL DISORDERS

(71) Applicant: UNIVERSITE DE LIEGE, Angleur (BE)

(72) Inventors: Jean-Michel Foidart, Liege (BE); Ekaterine Tskitishvili, Liege (BE)

(73) Assignee: UNIVERSITE DE LIEGE, Angleur (BE)

( * ) Notice: Subject to any disclaimer, the term of this patent is extended or adjusted under 35 U.S.C. 154(b) by 0 days.

(21) Appl. No.: 14/395,465

(22) PCT Filed: Apr. 8, 2013

(86) PCT No.: PCT/EP2013/057279
§ 371 (c)(1),
(2) Date: Oct. 17, 2014

(87) PCT Pub. No.: WO2013/156329
PCT Pub. Date: Oct. 24, 2013

(65) Prior Publication Data
US 2015/0133419 A1     May 14, 2015

(30) Foreign Application Priority Data
Apr. 19, 2012    (EP) ..................................... 12164741

(51) Int. Cl.
*A61K 31/565* (2006.01)
*A61K 31/567* (2006.01)

(52) U.S. Cl.
CPC ............. *A61K 31/567* (2013.01); *A61K 31/565* (2013.01)

(58) Field of Classification Search
CPC ........................... A61K 31/567; A61K 31/565
USPC .................................. 514/169, 182, 874, 903
See application file for complete search history.

(56) References Cited

FOREIGN PATENT DOCUMENTS

| WO | WO 03/103683 A1 | 12/2003 |
| WO | WO 2007/038636 A2 | 4/2007 |
| WO | WO 2008/156365 A1 | 12/2008 |
| WO | WO 2009/061428 A1 | 5/2009 |

OTHER PUBLICATIONS

Nunez et al. 2007 "17β-Estradiol protects the neonatal brain from hypoxia-ischemia", *Experimental Neurology* 208(2); 269-276.

*Primary Examiner* — Jennifer M Kim
(74) *Attorney, Agent, or Firm* — Knobbe, Martens, Olson & Bear, LLP

(57) ABSTRACT

The invention relates to the prophylactic and therapeutic applications of certain estrogenic components, such as estetrol, in neurological disorders, such as neonatal hypoxic-ischemic encephalopathy (HIE).

10 Claims, 20 Drawing Sheets

A

B

A

B

A

B

A

B

ESTROGENIC COMPONENTS FOR USE IN THE TREATMENT OF NEUROLOGICAL DISORDERS

FIELD OF THE INVENTION

The present invention is in the medical field. The invention more particularly relates to new medical uses of certain estrogenic components such as estetrol (1,3,5(10)-estratrien-3, 15α,16α,17β-tetrol).

BACKGROUND OF THE INVENTION

Neurological disorders, in particular central nervous system (CNS) disorders, encompass numerous afflictions, including inter alia acute CNS injury (e.g., hypoxic-ischemic encephalopathies, stroke, traumatic brain injury, spinal cord injury, cerebral palsy), neurodegenerative diseases (e.g., Alzheimer's disease, Parkinson's disease, frontotemporal dementia), and a large number of central nervous system dysfunctions (e.g. depression, epilepsy, and schizophrenia).

Neonatal hypoxic-ischemic encephalopathy (HIE) is a neurological disorder that causes damage to cells in the brain in neonates due to inadequate oxygen supply. Brain hypoxia and ischemia due to systemic hypoxemia and reduced cerebral blood flow (CBF) are primary reasons leading to neonatal HIE accompanied by gray and white matter injuries occurring in neonates. Neonatal HIE may cause death in the newborn period or result in what is later recognized as developmental delay, mental retardation, or cerebral palsy (CP). Even though different therapeutic strategies have been developed recently, neonatal HIE remains a serious condition that causes significant mortality and morbidity in near-term and term newborns and therefore, it remains a challenge for perinatal medicine.

Over the past several years, a rat model of hypoxic-ischemic brain damage became the most employed model in perinatal medicine. At post-natal day 7 (P7; day of birth=P1), the rats brain is histologically similar to that of a 32- to 34-week gestation human fetus or newborn infant, i.e., cerebral cortical neuronal layering is complete, the germinal matrix is involuting, and white matter as yet has undergone little myelination. In order to produce hypoxic-ischemic brain damage in the 7-day-old rat pups, they undergo unilateral common carotid artery ligation followed by systemic hypoxia produced by the inhalation of 8% oxygen/balance nitrogen, at constant temperature (37° C.) (Vanucci et al. 2005. Dev Neurosci, vol. 27, 81-86).

The rat model has proven to provide important information regarding underlying mechanisms of perinatal hypoxic-ischemic brain damage and how tissue injury can be prevented or minimized through therapeutic intervention. In particular, physiologic and therapeutic manipulations have been applied to the immature rat model of perinatal hypoxic-ischemic brain damage in order to evaluate potential treatments, including hypothermia, xenon treatment and erythropoietin administration.

Promising neuroprotective agents include antiepileptic drugs, erythropoietin, melatonin and xenon. Data from animal models of asphyxia further suggest that neurologic outcome after HIE can be improved by adding adjuvant therapies to hypothermia, beginning in the hours to days after insult. These promising treatments need now to be assessed in clinical trials. Phase 1-2 clinical studies using biomarker outcomes, e.g., phosphorous magnetic resonance spectroscopy, and involving small number of infants are key to assess safety and potential efficacy before new treatments are taken to pragmatic trials. Phase 1-2 trials of xenon and erythropoietin are already planned or underway.

Therapies for neurological disorders, in particular CNS injuries or neurodegenerative diseases, may center on protecting against brain or spinal cord damage or restoring nerve cell activity, e.g., through the use of neurotrophic factors. Neurothrophic factors, such as e.g., epidermal growth factor (EGF) and transforming growth factor-alpha (TGF-α), are polypeptides that variously support the survival, proliferation, differentiation, size, and function of nerve cells. Treatment of neurological disorders may also encompass the administration of stem cells to replace those neural cells lost by natural cell death, injury or disease.

A problem encountered with the administration of such neurotrophic factors or stem cells is the blood-brain barrier, which may impede their transfer from the blood flow into the CNS. Therefore, treatments often require the direct application of a neurotrophic factor or infusion of stem cells to a site of injury or damage in the CNS in a subject in need of such treatment.

Given the paucity of successful treatments for neurological disorders in general, there remains a need for additional therapeutic agents and methods, that preferably do not rely on invasive intracranial procedures or substances with improved blood-brain barrier passage.

SUMMARY OF THE INVENTION

The present invention addresses one or more of the above discussed needs in the art.

As shown in the experimental section, the inventors found that certain estrogenic components, exemplified by estetrol, have neuroprotective effects. For example, the inventors surprisingly demonstrated that treating rat pups with estetrol protected them against brain damage due to hypoxia-ischemia. Also notably, treatment of rat pups with certain estrogenic components, exemplified by estetrol, following (i.e., subsequent to) hypoxia-ischema was shown to result in less brain injury, corroborating that these compounds exhibit advantageous therapeutic effects. Furthermore, it was shown that treatment of rat pups with certain estrogenic compounds, exemplified by estetrol, promote neurogenesis and vasculogenesis.

Estetrol (E4) is an estrogenic steroid substance synthesized exclusively by the fetal liver during human pregnancy and reaching the maternal circulation through the placenta. It is found in maternal urine as early as 9 weeks of gestation, increasing substantially as pregnancy progresses (Holinka et al. 2008. J Steroid Biochem Mol Biol, vol. 110, 138-143). Unconjugated E4 is also found in amniotic fluid. Estetrol is a major metabolite of estradiol (E2), formed from its precursors via hydroxylation.

E4 is believed to be less potent compared to E2 due to its low estrogen receptor binding affinity compared to E2. Competitive receptor binding studies revealed low affinity binding of E4 to nuclear and cytosolic estrogen receptors relative to that of E2, showing values for cytosolic estrogen receptor binding of 1.0 and 0.015 for E2 and E4, respectively (Holinka et al. supra). E4 acts as a weak estrogen in growth promotion of cultured estrogen-responsive MCF-7 cells compared to E2: the potency of E2 was shown to be 50 times higher than E4.

Warmerdam et al. 2008 (Climacteric, vol. 11 (suppl. 1), 59-63) reported octanol-water partition (Pow) coefficient—which is a measure of the lipophilic or hydrophilic properties of a compound, expressed as logarithm of Pow or "Pow Log"—of estetrol, Pow Log=1.47 or 1.695, depending on experimental settings. Because Pow Log of 2.0 is considered optimal to allow the passage of compounds through the blood-brain barrier (Warmerdam et al. 2008, supra), the strong neuroprotective action of estetrol in the rat model of neonatal HIE is surprising.

Recent pharmacological and clinical data support the potential clinical use of E4 for applications such as hormone therapy, contraception, prevention of osteoporosis and menopausal hot flushes, cancer therapy, and treatment or prevention of cardiovascular pathologies. To our knowledge, no effects of estrogenic components illustrated by E4 in the central nervous system have been described so far.

Accordingly, in an aspect, the invention provides an estrogenic component selected from the group consisting of: estrogenic substances having the formula (I):

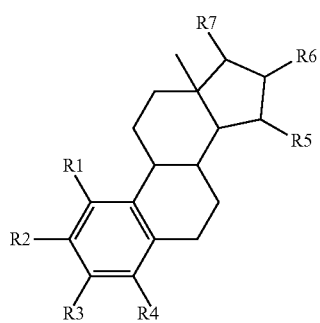

(I)

wherein $R_1$, $R_2$, $R_3$, $R_4$ each independently are a hydrogen atom, a hydroxyl group, or an alkoxy group with 1-5 carbon atoms; wherein each of $R_5$, $R_6$, $R_7$ is a hydroxyl group; and wherein no more than 3 of $R_1$, $R_2$, $R_3$, $R_4$ are hydrogen atoms;

precursors of the estrogenic substances; and mixtures of one or more of the estrogenic substances and/or the precursors;

for use in the treatment of a neurological disorder.

Preferably, the invention provides for an estrogenic component selected from the group consisting of:

estrogenic substances having the formula (I):

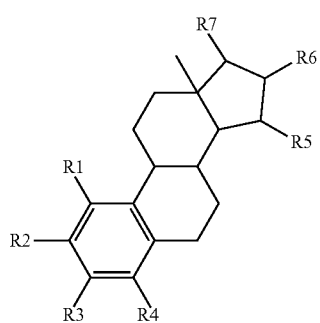

(I)

wherein $R_1$, $R_2$, $R_3$, $R_4$ each independently are a hydrogen atom, a hydroxyl group, or an alkoxy group with 1-5 carbon atoms; wherein each of $R_5$, $R_6$, $R_7$ is a hydroxyl group; and wherein no more than 3 of $R_1$, $R_2$, $R_3$, $R_4$ are hydrogen atoms;

precursors of the estrogenic substances, wherein the precursors are derivatives of the estrogenic substances, wherein the hydrogen atom of at least one of the hydroxyl groups has been substituted by an acyl radical of a hydrocarbon carboxylic, sulfonic or sulfamic acid of 1-25 carbon atoms; tetrahydrofuranyl; tetrahydropyranyl; or a straight or branched chain glycosydic residue containing 1-20 glycosidic units per residue; and mixtures of one or more of the estrogenic substances and/or the precursors; for use in the treatment of a neurological disorder.

The invention also provides a method for treating a neurological disorder in a patient in need of such treatment, comprising administering a therapeutically effective amount of the estrogenic component as taught herein to said patient.

The invention also provides use of the estrogenic component as taught herein for the manufacture of a medicament for the treatment of a neurological disorder.

In preferred embodiments $R_3$ represents a hydroxyl group or an alkoxy group with 1-5 carbon atoms, more preferably $R_3$ represents a hydroxyl group.

In preferred embodiments, at least 2, more preferably 3 of $R_1$, $R_2$, $R_3$ and $R_4$ represent hydrogen atoms. In particularly preferred embodiments, $R_1$, $R_2$ and $R_4$ represent hydrogen atoms.

In certain embodiments, $R_3$ represents a hydroxyl group or an alkoxy group with 1-5 carbon atoms, more preferably $R_3$ represents a hydroxyl group, and at least 1, more preferably at least 2, and even more preferably all 3 of the groups $R_1$, $R_2$ and $R_4$ represent hydrogen atoms.

In further preferred embodiments $R_1$, $R_2$ and $R_4$ represent hydrogen atoms and $R_3$, $R_5$, $R_6$ and $R_7$ are hydroxyl groups; hence, the estrogenic substance or the estrogenic component is 1,3,5(10)-estratrien-3,15,16,17-tetrol. In a particularly preferred embodiment, the estrogenic substance or the estrogenic component is 1,3,5(10)-estratrien-3,15α,16α,17β-tetrol (estetrol).

In preferred embodiments, the precursors are derivatives of the estrogenic substances, wherein the hydrogen atom of at least one of the hydroxyl groups has been substituted by an acyl radical of a hydrocarbon carboxylic, sulfonic or sulfamic acid of 1-25 carbon atoms; tetrahydrofuranyl; tetrahydropyranyl; or a straight or branched chain glycosydic residue containing 1-20 glycosidic units per residue.

As noted, the present invention provides for an estrogenic component as taught herein for use in the treatment of a neurological disorder.

In preferred embodiments, the invention provides for an estrogenic component as taught herein for use in the therapeutic treatment of a neurological disorder, i.e., treatment of a neurological disorder, wherein the estrogenic component is administered to a subject diagnosed with the neurological disorder.

With the term "neurological disorder" is generally meant a disorder affecting the nervous system, including the central nervous system and the peripheral nervous system.

In preferred embodiments, the neurological disorder is an injury, preferably a central nervous system injury, more preferably a brain injury, or is a neurodegenerative disease. Preferably, the neurological disorder is thus selected from the group comprising or consisting of a brain injury, a spinal cord injury, and a neurodegenerative disease. More preferably the neurological disorder is selected from the group comprising or consisting of a brain injury and a neurodegenerative disease.

In preferred embodiments, the neurological disorder is selected from the group comprising or consisting of hypoxic brain injury, anoxic brain injury, traumatic brain injury, Alzheimer's disease, and Parkinson's disease.

In certain embodiments, the Alzheimer's disease is early-stage Alzheimer's disease, i.e., pre-clinical stage or earliest clinical stages of Alzheimer's disease.

In certain embodiments, the Parkinson's disease is early-stage non-demented Parkinson's disease or Parkinson's disease with mild cognitive impairment.

With the terms "hypoxic injury" or "anoxic injury" is meant herein brain injury as a result of oxygen deprivation either due to hypoxic (i.e., a reduced supply of oxygen to the brain) or anoxic (i.e., a complete lack of oxygen to the brain) mechanisms, respectively.

Hypoxic/anoxic injuries may affect localized area(s) of the brain or the entire brain. In certain preferred embodiments, the hypoxic/anoxic/traumatic brain injuries affect at least the hippocampus or the cerebral cortex, e.g., at least the hippocampus and the cerebral cortex, preferably at least the hippocampus.

In preferred embodiments, the neurological disorder is a hypoxic-ischemic encephalopathy (HIE).

With the terms "hypoxic-ischemic encephalopathy" or "HIE" is specifically meant herein a condition that occurs when the entire brain is deprived of an adequate oxygen supply, but the deprivation is not total. The inadequate oxygen supply may be hypoxic in origin, i.e., reduced oxygen availability, and/or ischemic in origin, i.e., oxygen deprivation due to a disruption in blood flow. In certain preferred embodiments, the HIE affects at least the hippocampus or the cerebral cortex, e.g., at least the hippocampus and the cerebral cortex, preferably at least the hippocampus.

In particularly preferred embodiments, the estrogenic component as taught herein is used for the treatment of neonatal hypoxic-ischemic encephalopathy (HIE).

As used herein, the expression "treatment of neonatal HIE" may encompass protection against brain damage, and may further encompass the prevention of, alleviation of symptoms associated with, or diminishment of extent of neonatal HIE-related disorders, such as, e.g., developmental delay, mental retardation, or cerebral palsy (CP) (amelioration of CP includes for example improvement in motor, behavior, and/or cognitive function). As used herein, the term "cerebral palsy" refers to a group of conditions that are characterized by chronic disorders of movement or posture. Cerebral palsy may be accompanied by seizure disorders, sensory impairment and/or cognitive limitation.

The above and additional aspects, preferred embodiments and features of the invention are described in the following sections and in the appended claims. Each aspect, embodiment or feature described herein may be combined with any other aspect(s), embodiment(s) or feature(s) unless clearly indicated to the contrary. In particular, any feature specified herein, and particularly any feature indicated as being preferred or advantageous, may be combined with any other feature(s) specified herein, and particularly with any other feature(s) indicated as being preferred or advantageous. The subject matter of the appended claims is hereby specifically incorporated in this specification.

DETAILED DESCRIPTION OF THE INVENTION

Figure 1:
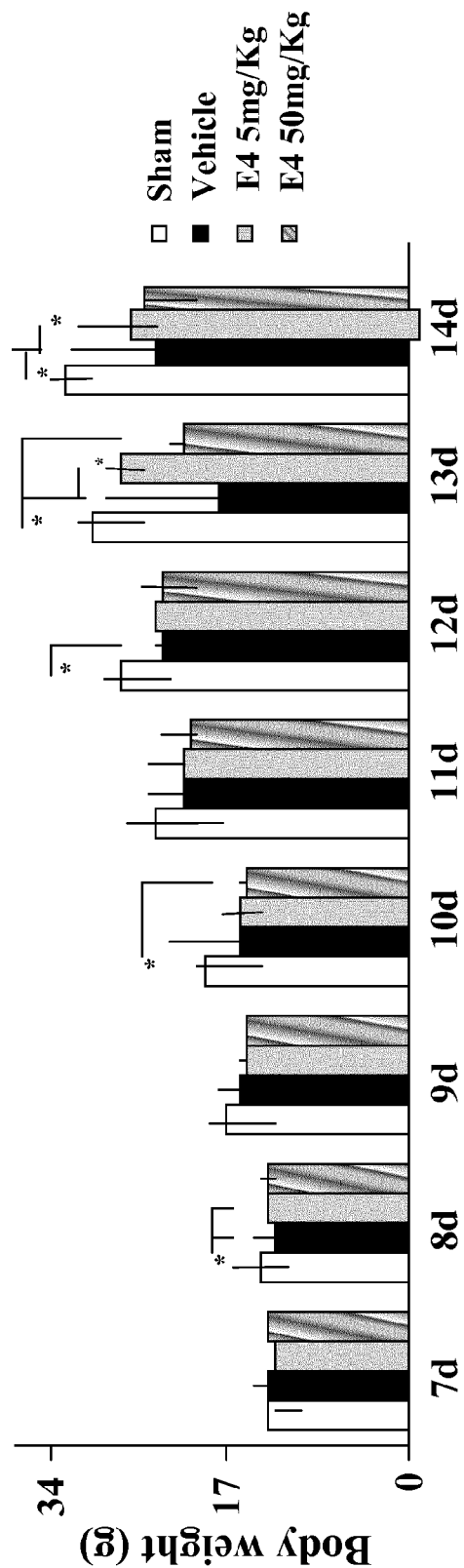
FIG. 1 Post-operative body weights of rat pups. Post-operative body weights of rat pups that were injected intraperitoneally from day 4 to day 7 including after delivery either by vehicle (saline solution) (Vehicle), 5 mg/kg E4 (E4 5 mg/kg) or 50 mg/kg E4 (E4 50 mg/kg) or not injected (Sham). Mean±SEM of body weights of 7 rat pups from the Sham group, 11 rat pups of Vehicle groups, 7 rat pups from the E4 5 mg/kg group and 5 rat pups from the E4 50 mg/kg group are shown.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The term also encompasses "consisting of" and "consisting essentially of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the term "one or more", such as one or more members of a group of members, is clear per se, by means of further exemplification, the term encompasses inter alia a reference to any one of said members, or to any two or more of said members, such as, e.g., any $\geq 3$, $\geq 4$, $\geq 5$, $\geq 6$ or $\geq 7$ etc. of said members, and up to all said members.

All documents cited in the present specification are hereby incorporated by reference in their entirety.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention. When certain terms are explained or defined in connection with a particular aspect or embodiment, such connotation is meant to apply throughout this specification, i.e., also for other aspects or embodiments, unless otherwise specified or unless the context clearly dictates otherwise.

The present inventors found that estetrol and related estrogenic components have neuroprotective effects, as illustrated in an established model of neonatal hypoxic-ischemic encephalopathy in rat pups. They also revealed that estetrol and related estrogenic components exhibit therapeutic effects as shown in the same rat model of neonatal hypoxic-ischemic encephalopathy. Furthermore, they found that estetrol and related estrogenic components induce or promote neurogenesis and vasculogenesis in the rat pups brain.

As used herein, the term "estrogenic component" refers to an estrogenic substance as taught herein, a precursor thereof or a mixture of one or more of said estrogenic substances and/or precursors.

In certain embodiments, the estrogenic component is selected from the group consisting of:
estrogenic substances having the formula (I), wherein $R_1$ is a hydrogen atom, a hydroxyl group, or an alkoxy group with 1-5 carbon atoms; wherein $R_2$ is a hydrogen atom, a hydroxyl group, or an alkoxy group with 1-5 carbon atoms; wherein $R_3$ is a hydrogen atom, a hydroxyl group, or an alkoxy group with 1-5 carbon atoms; wherein $R_4$ is a hydrogen atom, a hydroxyl group, or an alkoxy group with 1-5 carbon atoms; wherein $R_5$ is a hydroxyl group; wherein $R_6$ is a hydroxyl group; wherein $R_7$ is a hydroxyl group; and wherein no more than 3 of $R_1$, $R_2$, $R_3$, and $R_4$ are hydrogen atoms;

precursors of the estrogenic substances; and mixtures of one or more of the estrogenic substances and/or the precursors.

In certain embodiments, the estrogenic component is selected from the group consisting of:

estrogenic substances having the formula (I), wherein $R_1$ is a hydrogen atom, a hydroxyl group, or an alkoxy group with 1-5 carbon atoms; wherein $R_2$ is a hydrogen atom, a hydroxyl group, or an alkoxy group with 1-5 carbon atoms; wherein $R_3$ is a hydrogen atom, a hydroxyl group, or an alkoxy group with 1-5 carbon atoms; wherein $R_4$ is a hydrogen atom, a hydroxyl group, or an alkoxy group with 1-5 carbon atoms; wherein $R_5$ is a hydroxyl group; wherein $R_6$ is a hydroxyl group; wherein $R_7$ is a hydroxyl group; and wherein at least one of $R_1$, $R_2$, $R_3$, and $R_4$ is a hydroxyl group, or an alkoxy group with 1-5 carbon atoms;

precursors of the estrogenic substances; and mixtures of one or more of the estrogenic substances and/or the precursors.

In embodiments, the estrogenic component is selected from the group consisting of: estrogenic substances having the formula (III):

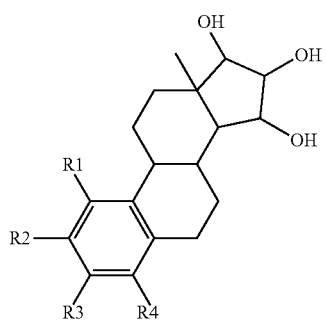

(III)

wherein $R_1$ is a hydrogen atom, a hydroxyl group, or an alkoxy group with 1-5 carbon atoms; wherein $R_2$ is a hydrogen atom, a hydroxyl group, or an alkoxy group with 1-5 carbon atoms; wherein $R_3$ is a hydrogen atom, a hydroxyl group, or an alkoxy group with 1-5 carbon atoms; wherein $R_4$ is a hydrogen atom, a hydroxyl group, or an alkoxy group with 1-5 carbon atoms; and wherein at least one of $R_1$, $R_2$, $R_3$, and $R_4$ is a hydroxyl group, or an alkoxy group with 1-5 carbon atoms;

precursors of the estrogenic substances; and mixtures of one or more of the estrogenic substances and/or the precursors.

The expression "alkoxy group with 1-5 carbon atoms" may also be denoted as "$C_{1-5}$alkoxy" or "$C_{1-5}$alkyloxy" and refers to a radical having the formula: —OR$^a$ wherein R$^a$ is $C_{1-5}$alkyl as defined herein. Non-limiting examples of suitable $C_{1-5}$alkyloxy include methyloxy, ethyloxy, propyloxy, isopropyloxy, butyloxy, isobutyloxy, sec-butyloxy, tert-butyloxy, and pentyloxy.

The estrogenic substances as taught herein are distinct from both the biogenic and synthetic estrogens that are commonly applied in pharmaceutical formulations in that the 5-membered ring in the steroid skeleton comprises at least 3 hydroxyl substituents rather than 0-2.

The estrogenic substances also encompass their stereoisomeric forms, their pharmaceutically acceptable addition salts, hydrates and solvates.

The estrogenic substances represented by formulas (I) and (III) encompass various enantiomers since the carbon atoms that carry hydroxyl-substituents, in particular $R_5$, $R_6$ and $R_7$, are chirally active. In preferred embodiments, the estrogenic substance is 15α-hydroxy substituted. In other preferred embodiments the substance is 16α-hydroxy substituted. In yet other preferred embodiments, the substance is 17β-hydroxy substituted. Most preferably the estrogenic substances are 15α,16α,17β-trihydroxy substituted. The other chirally active carbon atoms in the steroid skeleton of the estrogenic substances as taught herein preferably have the same configuration as the corresponding carbon atoms in 17β-estradiol and other biogenic estrogens.

Preferably, the estrogenic substances as used herein are so-called biogenic estrogens, i.e., estrogens that occur naturally in the human body. Because biogenic estrogens are naturally present in the fetal and female body, side-effects are not expected to occur, particularly not if the serum levels resulting from the exogenous administration of such estrogens do not substantially exceed naturally occurring concentrations.

In preferred embodiments, at least one, more preferably exactly one, of $R_1$, $R_2$, $R_3$, $R_4$ represents a hydroxyl group, meaning that the estrogenic substance contains at least 4, more preferably exactly 4, hydroxyl groups. In case the estrogenic substance contains 4 hydroxyl groups, it may also be denoted as a tetrahydroxylated estrogen.

Non-limiting examples of commercially available estrogens that contain at least 4 hydroxyl groups or their precursors are: 1,3,5(10)-estratrien-2,3,15α,16α,17β-pentol 2-methyl ether; 1,3,5(10)-estratrien-2,3,15β,16α,17β-pentol 2-methyl ether; 1,3,5(10)-estratrien-3,15α,16α,17β-tetrol; 1,3,5(10)-estratrien-3,15α,16α,17β-tetrol tetra acetate; or 1,3,5(10)-estratrien-3,15β,16β,17β-tetrol tetra acetate.

In particularly preferred embodiments, the estrogenic substance is 1,3,5(10)-estratrien-3,15,16,17-tetrol.

In further particularly preferred embodiments, the estrogenic substance is estetrol.

"Estetrol", "1,3,5(10)-estratrien-3,15α,16α,17β-tetrol" and "$E_4$" are synonyms and are used interchangeably herein to refer to an estrogenic compound, known to be produced in nature by the human fetal liver during pregnancy only. It is a tetrahydroxylated estrogen, characterized by the presence of four hydroxyl groups, hence its acronym $E_4$. Its general formula is represented by formula (II):

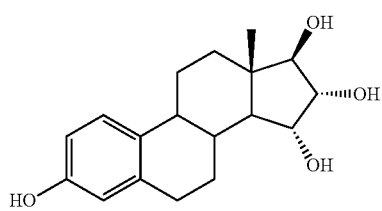

(II)

The invention also encompasses the use of precursors of the estrogenic substances as taught herein. These precursors are capable of liberating the estrogenic substances, in particular when used according to the invention, e.g., as a result of metabolic conversion.

Preferably, these precursors are derivatives of the estrogen substances, wherein the hydrogen atom of at least one of the hydroxyl groups has been substituted by an acyl radical of a hydrocarbon carboxylic, sulfonic or sulfamic acid of 1-25 carbon atoms; tetrahydrofuranyl; tetrahydropyranyl; or a straight or branched chain glycosydic residue containing 1-20 glycosidic units per residue.

Non-limiting examples of precursors which can suitably be used in accordance with the invention are esters that can be obtained by reacting the hydroxyl groups of the estrogen substances with substances that contain one or more carboxy ($M^{+-}OOC$—) groups, wherein $M^+$ represents a hydrogen or (akali) metal cation. Hence, particularly preferred examples of precursors are derivatives of the estrogen substances, wherein the hydrogen atom of at least one of the hydroxyl groups in formula (I) or (II) or (III) has been substituted by —CO—R, wherein R is a hydrocarbon radical comprising from 1-25 carbon atoms, preferably R is a hydrogen, or an alkyl, alkenyl, cycloalkyl or aryl radical comprising from 1-20 carbon atoms.

The term "alkyl", as a group or part of a group, refers herein to a hydrocarbyl radical of formula $C_nH_{2n+1}$ wherein n is a number ranging from 1 to about 25. Preferably, alkyl groups as intended herein comprise from 1 to 20 carbon atoms, such as from 1 to 10 carbon atoms, from 1 to 5 carbon atoms, from 1 to 4 carbon atoms, or from 1 to 3 carbon atoms, more preferably from 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-5}$alkyl means an alkyl of one to five carbon atoms. Examples of alkyl groups, in particular $C_{1-5}$alkyl groups, are methyl, ethyl, propyl, isopropyl, butyl, isobutyl, sec-butyl, tert-butyl, 2-methylbutyl, pentyl, iso-amyl and its isomers.

The term "alkenyl", as a group or part of a group, refers to an unsaturated hydrocarbyl group, which may be linear, or branched, comprising one or more carbon-carbon double bonds. Alkenyl groups may comprise at least 2 carbon atoms, such as from 2 to about 25 carbon atoms, and as used herein preferably from 2 to about 20 carbon atoms, such as from 2 to 10 carbon atoms, from 2 to 5 carbon atoms, from 2 to 4 carbon atoms, or from 2 to 3 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.

The term "cycloalkyl", as a group or part of a group, refers to a saturated or partially unsaturated hydrocarbyl radical having 1 (i.e., monocyclic) or more, such as 2 (i.e., bicyclic), cyclic structures. The further rings of multi-ring cycloalkyl radicals may be either fused, bridged and/or joined through one or more spiro atoms. Cycloalkyl groups may comprise independently 3 or more carbon atoms in a ring, such as from 3 to 25 carbon atoms, preferably from 3 to 20 carbon atoms, more preferably from 3 to 8 carbon atoms, such as 5, 6 or 7 carbon atoms. Preferably, cycloalkyl groups as intended herein refer to monocyclic cycloalkyl groups and comprise from 3 to 20 carbon atoms. Examples of monocyclic cycloalkyl radicals include cyclopropyl, cyclobutyl, cyclopentyl, cyclohexyl, and the like.

The term "aryl" as a group or part of a group refers to a polyunsaturated, aromatic hydrocarbyl group comprising a single aromatic ring (e.g., phenyl) or multiple (e.g., two, three or four) aromatic rings fused together (e.g., naphthyl) or linked covalently (e.g., biphenyl). Aryl groups comprise at least 6 carbon atoms and preferably 6 to about 20 carbon atoms, more preferably 6 to 10 carbon atoms in a ring. An aromatic ring in an aryl group may optionally include one or two additional rings (cycloalkyl, heterocyclyl and/or heteroaryl) fused thereto. Non-limiting examples of aryl comprise phenyl, biphenylyl, 5- or 6-tetralinyl, 1-, 2-, 3-, 4-, 5-, 6-, 7- or 8-azulenyl, naphthalen-1- or -2-yl, 4-, 5-, 6 or 7-indenyl, 1- 2-, 3-, 4- or 5-acenaphtylenyl, 3-, 4- or 5-acenaphtenyl, 1-, 2-, 3-, 4- or 10-phenanthryl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

As noted, the estrogenic components as taught herein are useful in the treatment of neurological disorders in subjects.

As used herein, the terms "treat" or "treatment" refer to both therapeutic treatment and prophylactic or preventative measures, wherein the object is to prevent or slow down (lessen) an undesired physiological change or disorder, such as the development of a neurological disorder. Beneficial or desired clinical results include, but are not limited to, prevention of a disorder, reducing the incidence of a disorder, alleviation of symptoms associated with a disorder, diminishment of extent of a disorder, stabilised (i.e., not worsening) state of a disorder, delay or slowing of progression of a disorder, amelioration or palliation of the state of a disorder, remission (whether partial or total), whether detectable or undetectable, or combinations thereof. "Treatment" can also mean prolonging survival as compared to expected survival if not receiving treatment.

In certain embodiments, the estrogenic components as taught herein may be used for the prophylactic or preventive treatment of a neurological disorder, i.e., wherein the subject is administered the estrogenic component while not being diagnosed (e.g., prior to being diagnosed) with the neurological disorder. For example, the subject may be considered at risk of contracting/developing the neurological disorder. Hence, such treatment is aimed at preventing the neurological disorder.

In preferred embodiments, the estrogenic components as taught herein may be used for the therapeutic treatment of a neurological disorder. Accordingly, in preferred embodiments, the invention relates to an estrogenic component as taught herein for use in the treatment of a neurological disorder, wherein the estrogenic component is administered to a subject diagnosed with the neurological disorder. Hence, such treatment is aimed at therapy of the existing neurological disorder.

As used herein, the terms "therapeutic treatment" or "therapy" and the like, refer to treatments wherein the object is to bring a subjects body or an element thereof from an undesired physiological change or disorder, such as a neurological disorder, to a desired state, such as a less severe or unpleasant state (e.g., amelioration or palliation), or back to its normal, healthy state (e.g., restoring the health, the physical integrity and the physical well-being of a subject), to keep it (i.e., not worsening) at said undesired physiological change or disorder (e.g., stabilization), or to prevent or slow down progression to a more severe or worse state compared to said undesired physiological change or disorder.

Except when noted, "subject" or "patient" are used interchangeably and refer to animals, preferably warm-blooded animals, more preferably vertebrates, even more preferably mammals, still more preferably primates, and specifically include human patients and non-human mammals and primates. "Mammalian" subjects refer to any animal classified as such and include, but are not limited to, humans, domestic animals, commercial animals, farm animals, zoo animals, sport animals, pet and experimental animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. Preferred patients are human subjects.

As used herein, a phrase such as "a subject in need of treatment" includes subjects that would benefit from treatment, preferably therapeutic treatment, of a recited disorder, in particular a neurological disorder. Such subjects may include, without limitation, those that have been diagnosed with said disorder, those prone to contract or develop said disorder and/or those in whom said disorder is to be prevented. Particularly intended are patients diagnosed with a neurological disorder or in whom a neurological disorder is to be prevented.

As used herein, the term "diagnosis" refers to establishing and concluding that a subject is affected by a recited disorder, in particular a neurological disorder. The diagnosis may be based on the examination of symptoms associated with a recited disorder (such as, e.g., clinical diagnosis). Alternatively or in addition, the diagnosis may be made before the symptoms can be examined (i.e., preclinical diagnosis) or because the symptoms are mild or not confined to a recited disorder through, e.g., detecting biomarkers indicative for the recited disorder and/or imaging techniques.

The term "therapeutically effective amount" as used herein refers to an amount of an estrogenic component or a pharmaceutical composition as taught herein effective to treat a neurological disorder in a subject, i.e., to obtain a desired local or systemic effect and performance. The term thus refers to the quantity of estrogenic component or pharmaceutical composition that elicits the biological or medicinal response in a tissue, system, animal, or human that is being sought by a researcher, veterinarian, medical doctor or other clinician. In particular, the term refers to the quantity of estrogenic component or pharmaceutical composition as taught herein which is necessary to prevent, cure, ameliorate, or at least minimize the clinical impairment, symptoms, or complications associated with a neurological disorder in either a single or multiple doses.

As used herein, the expression "treatment of a neurological disorder", such as therapeutic treatment of a neurological disorder, may encompass protecting against or preventing brain damage, including disruption of brain cell integrity and/or loss of brain cell structure or function, diminishing the extent of brain damage, not worsening brain damage or restoring brain damage, and may further encompass inducing or promoting neurogenesis and/or vasculogenesis.

In certain embodiments, the treatment of the neurological disorder, such as the therapeutic treatment of the neurological disorder, comprises protecting against brain damage, diminishing the extent of brain damage, not worsening brain damage or restoring brain damage. In particular embodiments, the therapeutic treatment of the neurological disorder comprises not worsening brain damage or restoring brain damage.

In embodiments, the treatment of the neurological disorder, such as the therapeutic treatment of the neurological disorder, comprises promoting neurogenesis, vasculogenesis, or neurogenesis and vasculogenesis.

Non-limiting examples for examining brain damage, neurogenesis and vasculogenesis include imaging techniques, in particular neuroimaging techniques, and detection and measurement of suitable biological markers in e.g. blood serum or cerebrospinal fluid. Suitable neuroimaging techniques include magnetic resonance imaging (MRI) and positron emission tomography (PET). Suitable biological markers for brain damage include for example S100B and glial fibrillary acidic protein (GFAP). Techniques for detecting and measuring biological markers in body fluids are well-known and include, for example, enzyme-linked immunosorbent assays (ELISAs).

As used herein, the term "neurological disorder" refers to any neurological disease, neurological condition, neurological behavior, and/or any symptom related thereto, affecting the central nervous system and/or the peripheral nervous system.

Preferably, the neurological disorder may affect the central nervous system, including brain and spinal cord, more preferably it may affect at least the brain, even more preferably it may affect at least the hippocampus, such as at least the hippocampus and the cortex.

The terms "hippocampus" and "hippocampal formation" are used as synonyms herein and refer to a brain region located in the medial temporal lobe of the brain that is involved in memory, and spatial memory and navigation. Mammals have two hippocampi, in each side of the brain and the term encompasses both hippocampi. As used herein, hippocampus refers to dentate gyrus (DG), cornu ammonis (CA) and subiculum. The dentate gyrus encompasses the fascia dentata, the hilus, the subgranular zone (SGZ), the granule cell layer, and the molecular layer. The subgranular zone (SGZ) is a narrow layer of cells located between the granule cell layer and the hilus of the DG. Cornu ammonis (CA) is differentiated into the fields cornu ammonis 1 (CA1), cornu ammonis 2 (CA2), cornu ammonis 3 (CA3), and cornu ammonis 4 (CA4). The neurological disorder may affect at least one, more than one or all of these regions, such as in particular, at least one, more than one or all of dentate gyrus, cornu ammonis 1, cornu ammonis 2, cornu ammonis 3, or subgranular zone.

The terms "cortex" and "cerebral cortex" are used as synonyms herein and generally denote the outermost sheet of neural tissue of the cerebrum. Cortex may be generally seen as composed of sensory, motor, and association areas.

The neurological disorder may affect the cortex, such as any region of the cortex, and in particular may affect the primary somatosensory cortex, more particularly the primary trunk region of the primary somatosensory cortex attached to the primary motor cortex.

Neurological disorders to be treated using the estrogenic components or pharmaceutical compositions taught herein may involve neuronal dysfunction and/or degeneration, damage or loss. Preferably, the neurological disorders to be treated involve neuronal degeneration, damage or loss, such as, for example, but without limitation, brain injuries, spinal cord injuries, or neurodegenerative diseases.

Exemplary brain injuries include, but are not limited to, hypoxic/anoxic brain injuries, including hypoxic-ischemic encephalopathy (HIE) such as preferably neonatal HIE, and further brain ischemia, or stroke, or traumatic brain injury.

Preferably, the brain injury, such as hypoxic brain injury, anoxic brain injury, or traumatic brain injury, affects at least the hippocampus, more preferably the brain injury disrupts brain cell integrity in at least the hippocampus.

Exemplary injuries to the spinal cord and associated ganglia include, but are not limited to, post-polio syndrome, traumatic injury, surgical injury, or paralytic diseases.

With the term "neurodegenerative disease or disorder" is generally meant a neurological disorder characterized by the progressive loss of structure or function of neurons, including death of neurons.

Preferred exemplary neurodegenerative diseases include, but are not limited to diseases characterized by the progressive loss of structure or function of neurons in the hippocampus and/or cortex, such as Alzheimer's Disease (AD), Parkinson's Disease (PD), frontotemporal dementia (FD) (which covers a range of conditions, including Pick's disease, frontal lobe degeneration), amyotrophic lateral sclerosis (ALS); diseases characterized by the progressive loss of structure or function of neurons, including death of neurons in the basal ganglia (in particular subthalamic nucleus, substantia nigra, and globus pallidus), brainstem (in particular the portion of the midbrain where the supranuclear eye movement resides), dentate nucleus of the cerebellum, such asprogressive supranuclear palsy, striatonigral degeneration, corticobasal degeneration, olivopontocerebellar atrophy, and the like.

Other examples of neurodegenerative diseases include, but are not limited to, Alzheimer's Disease (AD), Parkinson's Disease (PD), frontotemporal dementia (FTD), amyotrophic lateral sclerosis (ALS), Huntington's Disease (HD) and other polyglutamine expansion diseases, Pick's disease, progressive supranuclear palsy, striatonigral degeneration, corticobasal degeneration, olivopontocerebellar atrophy, Leigh's disease, infantile necrotizing encephalomyelopathy, Hunter's disease, mucopolysaccharidosis, various leukodystrophies (such as Krabbe's disease, Pelizaeus-Merzbacher disease and the like), amaurotic (familial) idiocy, Kuf's disease, Spielmayer-Vogt disease, Tay Sachs disease, Batten disease, Jansky-Bielschowsky disease, Reye's disease, cerebral ataxia, chronic alcoholism, beriberi, Hallervorden-Spatz; syndrome, cerebellar degeneration, and the like.

Preferably, the neurodegenerative disease is Alzheimer's Disease (AD) or Parkinson's Disease (PD).

In Alzheimer's disease, the hippocampus is one of the first regions of the brain to suffer damage (Hampel et al. 2008. Alzheimer & Dementia 4: 38-48). The estrogenic components or pharmaceutical compositions as taught herein may therefore in certain embodiments be particularly suitable for treating, in particular therapeutically treating, subjects in the earliest stages of AD, such as in the pre-clinical stage or earliest clinical stages of AD. Accordingly, in certain preferred embodiments, the neurological disorder to be treated is early-stage AD (i.e., pre-clinical stage or earliest clinical stages of AD).

Also Parkinson's disease is correlated with hippocampal damage. In particular, hippocampal atrophy was observed in patients with early-stage non-demented PD exhibiting impaired memory (Brück et al. 2004. J Neurol Neurosurg Psychiatry 75: 1467-1469) and in patients with PD who have mild cognitive impairment or dementia (Camicioli et al. 2003. Mov Disorder 18: 784-790). Accordingly, in certain preferred embodiments, the neurological disorder to be treated is early-stage non-demented PD or PD with mild cognitive impairment (MCI).

Further preferred exemplary neurological disorders that may be treated using the estrogenic components or pharmaceutical compositions taught herein may include but are not limited to: demyelinating autoimmune disorders, such as multiple sclerosis; neurological deficits caused by infection of inflammatory diseases or infectious, viral diseases of the central nervous system (CNS), such are AIDS encephalopathy, post-encephalitic Parkinsonism, viral encephalitis, bacterial meningitis or other CNS effects of infectious diseases; cortical sensory perception disorders, such as vestibular function disorders, balance and coordination disorders, dizziness, gait problems, dyslexia, clumsiness, audition discrimination and modulation disorders, vision problems, eye movement and coordination disorders, or sensory disturbance as symptoms of neurological diseases; bowel function disorders such are constipation or incontinence; and urinary bladder control disorders, such is urinary incontinence, as symptoms of CNS diseases; respiratory dysfunctions following cerebral palsy; autonomic neural function disorders that cause abnormal blood flow to the skin, abnormal sexual response, erectile dysfunction, headaches, neck pain, back pain, encephalomyelopathy in the setting of trauma, postural orthostatic tachycardia, orthostatic intolerance, orthostatic hypotension, syncope, neurogenic bowel, and neurogenic bladder.

exemplary neurological disorders that may be treated using the estrogenic components or pharmaceutical compositions taught herein may include but are not limited to: demyelinating autoimmune disorders, such as multiple sclerosis; neurological deficits caused by infection of inflammatory diseases, such as Creutzfeldt-Jacob disease or other slow virus infectious diseases of the central nervous system (CNS), AIDS encephalopathy, post-encephalitic Parkinsonism, viral encephalitis, bacterial meningitis or other CNS effects of infectious diseases; cortical motor function disorders, such as spasticity, paresis, clones, or hyperreflexia; cortical sensory perception disorders, such as vestibular function disorders, balance and coordination disorders, dizziness, gait problems, dyslexia, clumsiness, development delay, audition discrimination and modulation disorders, delayed and mechanical speech disorders, vision problems, eye movement and coordination disorders, or sensory disturbance disorders; lower cranial nerve dysfunctions, such as lack of coordination between speech, swallowing or smooth articulation; bowel function disorders, such as gastro-esophageal sphincter control problems; abnormal urinary functioning, such as enuresis, bedwetting, or urinary bladder control disorders; respiratory dysfunctions, such as excessive snoring, obstructive or central apnea, or abnormal respiratory response to oxygen and carbon dioxide levels; sleep-disordered breathing, such as sleep apnea, muscular dysfunction, or sudden infant death; developmental disorders, such as Chiari Malformation; or congenital diseases, such as Down's Syndrome, Morquio's syndrome, spondyloepiphysial dysplasia, achondroplasia, or osteogenesis; neurological behavioral disorders, such as attention deficit hyperactivity disorder, psychological problems, including anxiety, bipolar disorder, scizophrenia, or depression, autism spectrum disorders, including autism, Asperger Syndrome, and pervasive behavioral disorders-not otherwise specified; anatomic conditions, such as platybasia, retroflexed odontoid, basilar invagination, and foramen magnum stenosis; acquired bone-softening conditions, such as Rickets, Paget's disease, or hyperparathyroidism; metabolic bone disorders; connective tissue disorders, including hypermobility connective tissue disorders, such as Ehlers Danlos Syndrome; cervico-medullary syndrome; renal, metabolic, or endocrine syndromes; autonomic neural function disorders that cause abnormal blood flow to the skin, abnormal sexual response, GERDS, dyspraxia, idiopathic scoliosis, headaches, neck pain, back pain, head pain, encephalomyelopathy in the setting of trauma, neoplasm, positional orthostatic tachycardia, and bulbar findings.

As shown in the experimental section, the estrogenic components as taught herein exhibit therapeutic effects on brain damage and promote neurogenesis and vasculogenesis after hypoxia-ischemia. Accordingly, the estrogenic components or pharmaceutical compositions as taught herein may be suitable for treating hypoxic brain injury, anoxic brain injury and/or traumatic brain injury, wherein the estrogenic component or pharmaceutical composition is administered after hypoxia, ischemia and/or trauma. In particular, the estrogenic components or pharmaceutical compositions as taught herein may be suitable for treating hypoxic-ischemic encephalopathy, such as preferably neonatal hypoxic-ischemic encephalopathy, wherein the estrogenic component or pharmaceutical composition is administered after hypoxia-ischemia (i.e., therapeutic treatment of HIE). Preferably, the estrogenic component or pharmaceutical composition is administered as early as possible after hypoxia, ischemia, trauma or hypoxia-ischemia, such as within 12 hours, 9 hours, or 6 hours after hypoxia, ischemia, trauma or hypoxia-ischemia, more preferably within 6 hours, such as within 5 hours, 4 hours, 3 hours, 2 hours, 1 hour, 30 minutes or 15 minutes, after hypoxia, ischemia, trauma or hypoxia-ischemia, in subjects such as in human subjects.

As noted above, the estrogenic components or pharmaceutical compositions as taught herein may also be particularly suitable for the treatment of AD. For example, the estrogenic components or pharmaceutical composition as taught herein may be suitable for the prophylactic or preventive treatment of AD, wherein the estrogenic component or the pharmaceutical composition is administered to menopausal women with a familial history of AD. The estrogenic components or pharmaceutical composition as taught herein may also be suitable for the therapeutic treatment of early-stage AD, wherein the estrogenic component or the pharmaceutical composition is administered to a patient diagnosed with early-stage AD.

Diagnosis of early-stage AD may be achieved by, e.g., neuroimaging, such as MRI, whereby early-stage AD patients are characterized by atrophy of the hippocampal formation (Hampel et al. 2008. supra). Alternatively or in addition, early-stage AD diagnosis may be established on the basis of evaluating biomarkers, such as, e.g., amyloid beta 42 (Aβ42), amyloid beta 40 ratio (Aβ40), total tau protein, hyperphosphorylated tau protein, β-secretase (BACE), or any combination thereof, in the cerebrospinal fluid (Hampel et al. 2008. supra).

As noted above, the estrogenic components or pharmaceutical compositions as taught herein may also be particularly suitable for the treatment of early-stage non-demented PD or PD with mild cognitive impairment (MCI), more preferably therapeutic treatment of early-stage non-demented PD or PD with mild cognitive impairment, wherein the estrogenic component or the pharmaceutical composition is administered to a patient diagnosed with early-stage non-demented PD, in particular a patient diagnosed with early-stage non-demented PD who exhibits impaired memory, or a patient diagnosed with PD who has MCI.

Diagnosis of patients with early-stage non-demented PD may be based on the examination of clinical symptoms of PD, whereby patients with early-stage non-demented PD have at least two of the PD symptoms selected from the group consisting of tremor, rigidity, and hypokinesia, optionally in combination with neuroimaging techniques such as, e.g., MRI. Volumetric MRI imaging might provide an early marker for dementia in PD, whereby patients with early-stage non-demented PD and PD patients who have mild cognitive impairment are characterized by atrophy of the hippocampus. Impaired memory can be evaluated through neuropsychological tests, such as for example the Wechsler Memory Scale-Revised test for verbal memory (VEM).

The estrogenic components taught herein may be used alone or in combination with any of the known therapies for neurological disorders ("combination therapy").

Combination therapies as contemplated herein may comprise the administration of at least one estrogenic component as taught herein and at least one other pharmaceutically or biologically active ingredient. Said estrogenic component(s) and said pharmaceutically or biologically active ingredient(s) may be administered in either the same or separate pharmaceutical composition(s), simultaneously, separately or sequentially in any order.

The at least one "other pharmaceutically or biologically active ingredient" particularly refers to a substance other than the estrogenic components described herein which is effective to treat a neurological disorder and which may or may not lead to a synergistic effect with the estrogenic component. Non-limiting examples of pharmaceutically or biologically active ingredients suitable for combined administration with the estrogenic components taught herein, particularly for use in the treatment of HIE such as preferably neonatal HIE, include antiepileptic drugs, erythropoietin, melatonin and xenon.

Also contemplated herein is the combination of the administration of at least one estrogenic component as taught herein with moderate hypothermia (i.e., reducing the body temperature to 33° C. to 34° C.). Such combination therapy may be particularly suitable for treating, preferably therapeutically treating, hypoxic-ischemic encephalopathy (HIE) such as preferably neonatal HIE.

The estrogenic components as disclosed herein may be formulated into pharmaceutical compositions or formulations with one or more pharmaceutically acceptable carriers/excipients. The pharmaceutical compositions may comprise one or more estrogenic components as disclosed herein. The pharmaceutical compositions may also further comprise one or more other pharmaceutically or biologically active ingredients as defined above. Accordingly, also disclosed herein is a pharmaceutical composition comprising an estrogenic component as disclosed herein.

The term "pharmaceutically acceptable" as used herein is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline, phosphate buffered saline, or optionally Tris-HCl, acetate or phosphate buffers), solubilisers (such as, e.g., Tween 80, Polysorbate 80), colloids, dispersion media, vehicles, fillers, chelating agents (such as, e.g., EDTA or glutathione), amino acids (such as, e.g., glycine), proteins, disintegrants, binders, lubricants, wetting agents, stabilisers, emulsifiers, sweeteners, colorants, flavourings, aromatisers, thickeners, agents for achieving a depot effect, coatings, antifungal agents, preservatives (such as, e.g., Thimerosal™, benzyl alcohol), antioxidants (such as, e.g., ascorbic acid, sodium metabisulfite), tonicity controlling agents, absorption delaying agents, adjuvants, bulking agents (such as, e.g., lactose, mannitol) and the like. The use of such media and agents for formulating pharmaceutical compositions is well known in the art. Except insofar as any conventional media or agent is incompatible with the active ingredient(s), its use in the therapeutic compositions may be contemplated. Suitable pharmaceutical carriers are described inter alia in Remington's Pharmaceutical Sciences, 18th ed., Mack Publishing Co., Easton, Pa. (1990).

The pharmaceutical composition can be prepared in a manner known per se to one of skill in the art. For this purpose, at least one estrogenic component as disclosed herein, one or more solid or liquid pharmaceutical excipients and, if desired, in combination with one or more other pharmaceutically or biologically active ingredients as defined above, are brought into a suitable administration form or dosage form which can then be used as a pharmaceutical in human medicine or veterinary medicine. The precise nature of the carrier or excipient or other material will depend on the route of administration. Such suitable administration forms—which may be solid, semi-solid, or liquid, depending on the manner of administration—as well as methods and carriers for use in the preparation thereof, will be clear to the skilled person; reference is made to for instance standard handbooks, such as Remington's Pharmaceutical Sciences (supra).

For example, the pharmaceutical composition as taught herein may be administered parenterally (such as by intravenous, intracerebral, intracerebroventricular, intramuscular, or subcutaneous injection, or intravenous infusion) in the form of a parenterally acceptable aqueous solution, which is pyrogen-free and has suitable pH, isotonicity and stability. Alternatively, the pharmaceutical composition as taught herein may be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories, percutaneous or topically (including ocular administration), for example in the form of ointments, tinctures, sprays or transdermal therapeutic systems (such as, e.g. a skin patch), or by inhalation in the form of nasal sprays or aerosol mixtures, or, for example, in the form of microcapsules, implants or rods.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiological sodium chloride solution, alcohols such as ethanol, glycerol, polyols, sucrose, invert sugar, glucose, mannitol, vegetable oils, etc. It is also possible to lyophilize the active ingredient(s) and to use the resulting lyophilisates, for example, for preparing preparations for injection or infusion. Suitable carriers for microcapsules, implants or rods are, for example, copolymers of glycolic acid and lactic acid.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate, and lactose and/or other excipients, binders, extenders, disintegrants, diluents, and lubricants known in the art.

The oral administration of a pharmaceutical composition comprising at least one estrogenic component as disclosed herein, is suitably accomplished by uniformly and intimately blending together a suitable amount of said component in the form of a powder, optionally also including a finely divided solid carrier, and encapsulating the blend in, for example, a hard gelatin capsule. The solid carrier can include one or more substances, which act as binders, lubricants, disintegrating agents, coloring agents, and the like. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Compressed tablets containing the pharmaceutical composition described herein can be prepared by uniformly and intimately mixing the active ingredient(s) with a solid carrier such as described above to provide a mixture having the necessary compression properties, and then compacting the mixture in a suitable machine to the shape and size desired. Molded tablets maybe made by molding in a suitable machine, a mixture of powdered active ingredient(s) moistened with an inert liquid diluent.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions, or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the estrogenic component(s) described herein, if desired with the substances customary therefore such as solubilizers, emulsifiers, or further auxiliaries, are brought into solution, suspension, or emulsion. The active ingredient(s) can also be lyophilized and the lyophilizates obtained used, for example, for the production of injection or infusion preparations. Suitable solvents are, for example, water, physiological saline solution, or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents, or solvents, such as mannitol, 1,3-butanediol, water, Ringer's solution, or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the estrogenic component described herein with a suitable non-irritating excipient, such as cocoa butter, synthetic glyceride esters, or polyethylene glycols, which are solid at ordinary temperatures, but liquefy and/or dissolve in the rectal cavity to release the drug.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying, and suspending agents, dispersing agents, desintegrants, bulking agents, fillers, preserving agents, sweetening agents, flavoring agents, flow regulators, release agents, etc.

The pharmaceutical compositions may be formulated so as to provide rapid, sustained, or delayed release of the active ingredient(s) contained therein, for example using liposomes or hydrophilic polymeric matrices based on natural gels or synthetic polymers.

The dosage or amount of the estrogenic component as disclosed herein used, optionally in combination with one or more other pharmaceutically or biologically active ingredients as defined above, depends on the individual case and is, as is customary, to be adapted to the individual circumstances to achieve an optimum effect. Thus, it depends on the nature and the severity of the disorder to be treated, and also on the sex, age, body weight, diet, general health, individual responsiveness of the human or animal to be treated, on the efficacy, metabolic stability and duration of action of the components used, on mode and time of administration, rate of excretion, on whether the therapy is acute or chronic or prophylactic, or on whether other pharmaceutically or biologically active ingredients as defined above are administered, or other therapies applied, in addition to the estrogenic component.

Without limitation, depending on the type and severity of the disorder, a typical daily dosage might range from about 1 µg/kg to about 250 mg/kg body weight or more, such as from about 1 µg/kg to about 100 mg/kg body weight, from about 1 µg/kg to about 50 mg/kg body weight, from about 1 µg/kg to about 10 mg/kg body weight, from about 1 µg/kg to about 1 mg/kg body weight, from about 1 µg/kg to about 0.4 mg/kg body weight or from about 5 µg/kg to about 0.4 mg/kg body weight, depending on the factors mentioned above. Preferably, the daily dosage may range from about 0,5 mg/kg to about 100 mg/kg body weight, more preferably from about 1 mg/kg to about 50 mg/kg body weight, even more preferably from about 2 mg/kg to about 25 mg/kg body weight, such as about 5 mg/kg body weight or 10 mg/kg body weight.

For repeated administrations over several days or longer, depending on the condition, the treatment is sustained until a desired suppression of disease symptoms occurs. A preferred dosage of the estrogenic component may be in the range from about 0,05 mg/kg to about 100 mg/kg body weight, more preferably from about 0.1 mg/kg to about 50 mg/kg body weight, even more preferably from about 1 mg/kg to about 20 mg/kg body weight. Thus, one or more doses of about 0.1 mg/kg, 0.5 mg/kg, 1 mg/kg, 2 mg/kg, 5 mg/kg, 10 mg/kg or 20 mg/kg (or any combination thereof) may be administered to the patient Other available dosages may be in the range from about 0.01 to about 20 mg/kg, such as from about 0.05 mg/kg to about 10 mg/kg. Thus, one or more doses of about 0.1 mg/kg, 0.2 mg/kg, 0.3 mg/kg, 0.4 mg/kg, 0.5 mg/kg, 1.0 mg/kg, 2.0 mg/kg, 4.0 mg/kg or 10 mg/kg (or any combination thereof) may be administered to the patient. Such doses may be administered as a single daily dose, divided over one or more daily doses, or essentially continuously, e.g., using a drip infusion, or intermittently, e.g., every week or every three weeks.

The pharmaceutical preparations disclosed herein are preferably in a unit dosage form, and may be suitably packaged, for example in a box, blister, vial, bottle, sachet, ampoule, or in any other suitable single-dose or multi-dose holder or container (which may be properly labeled); optionally with one or more leaflets containing product information and/or instructions for use. Generally, such unit dosages will contain between 1 and 1000 mg, such as between 5 and 500 mg, of at least one estrogenic component of the invention, e.g., about 10, 25, 50, 100, 200, 300, 400, 500, 600, 700, 800, 900 or 1000 mg per unit dosage.

Depending on the mode of administration, the pharmaceutical composition will preferably comprise from 0.05 to 99% by weight, more preferably from 0.1 to 70% by weight, even more preferably from 0.1 to 50% by weight of the estrogenic component as described herein, and, from 1 to 99.95% by weight, more preferably from 30 to 99.9% by weight, even more preferably from 50 to 99.9% by weight of a pharmaceutically acceptable carrier, all percentages being based on the total weight of the composition.

The pharmaceutical compositions can be administered separately at different times during the course of therapy or concurrently in divided or single combination forms. The present disclosure embraces all such regimes of simultaneous or alternating treatment and the term "administering" is to be interpreted accordingly.

The administration may be performed with food, e.g., a high-fat meal. The term "with food" means the consumption of a meal either during or no more than about one hour before or after administration of a pharmaceutical composition as described herein.

EXAMPLES

Example 1

Experimental Procedures

Study Animals:

Sprague-Dawley pregnant rats were obtained from Janvier (France). After delivery newborn rat pups were housed with their dams and reared normally at room temperature (25° C.) under a 12-hour light-dark cycle. All experimental protocols were approved by the University of Liege Ethical Committee. All efforts were made to minimize animal suffering.

In Vivo Manipulations:

Newborn rat pups were assigned to Sham group, Vehicle group, or E4 group.

Estetrol (E4) was dissolved in saline solution at different concentrations and an equal volume (5 µl/g) of the solution was injected intraperitoneally into the pups from the E4 group(s). Rat pups from the Vehicle group were intraperitoneally injected a saline solution. Rat pups from the Sham group were not injected at all.

Ischemia was produced by surgery encompassing left common carotid artery double ligation and cut; hypoxia was produced by the inhalation of 11%-8% of oxygen balanced by nitrogen at decreased concentration of oxygen for 20 minutes, followed by inhalation of 8% oxygen and 92% nitrogen at constant concentration for 35 minutes. The Sham group did not undergo hypoxic-ischemic insult.

All manipulations were performed at 37° C.

Measurement of Rat Pups Rectal Temperature:

The rectal temperature of the rat pups was measured with a multipurpose thermometer (BAT-10R, Physitemp Instruments Inc., Clifton, N.J., US) along with a rectal probe (RET-4, BioMedical Instruments, Zollnitz, Germany) at 0, 2, and 4 hours after exposure to hypoxic insult. To keep the variability of the temperature low, measurements of rectal temperature were made in a 25° C. room 15 min after removal of the pups from the nest (except the 1st post-hypoxic measurement which was done immediately). It has been shown that the rectal temperature corresponds very well to the brain core temperature (Thoresen et al. 1996. Arch Dis Child Fetal Neonatal 74: F3-F9, Yager et al. 1993. Pediatr Res 34: 525-529).

Preparation of Blood and Brain Samples:

The rat pups were sacrificed at postnatal day 14. Animals were deeply anesthetized with an overdose of sodium pentobarbital (100 mg/kg, ip).

Blood was withdrawn, centrifuged and the serum samples were stored at −80° C.

Animals were then perfused transcardially with 0.9% saline solution at 4° C., and then with 4% paraformaldehyde in a 0.1-mol/L phosphate-buffered saline solution (pH 7.4) at 4° C. The brains were quickly isolated, weighed and immersed in the same fixative solution at 4° C. for 24 hours, dehydrated with a graded series of ethanol and xylene, and embedded in paraffin.

Hematoxylin-Eosin Staining (Histochemistry):

Paraformaldehyde-fixed paraffin embedded samples of the removed brains were coronally sectioned at the same level of the hippocampus region in accordance to the Paxinos rat brain atlas (Paxinos and Watson 2007. In: The rat brain in stereotaxic coordinates, $6^{th}$ edition). Thickness of sections was 5 µm. Hematoxylin-eosin staining was performed. Briefly, sections were deparaffinized in xylene and rehydrated in graded ethanol concentrations before staining. Slides were stained with hematoxylin, rinsed for a few seconds in water, then placed in 1% eosin and washed, dehydrated, and coverslipped.

Intact Cell Counting:

Intact cell counting was performed on hematoxylin-eosin-stained sections of the rat pups brains at magnification 400× in 3 fields of the respective brain area. Countings were performed in cortex and hippocampus (regions: dentate gyrus (DG), subgranular zone (SGZ), cornu ammonis (CA1, CA2/CA3)). The sections were analyzed with the aid of a microscope (Olympus BX51, Olympus, Tokyo, Japan), an image scanner (DotSlide Digital Virtual Microscopy, Olympus, Germany) and ImageJ software (NIH, US).

Intact cells are uninjured. Injured cells are characterized by a pale eosinophilic staining along with non-uniform nuclear densities-shrunken, condensed, or pale and enlarged.

Microtubule-Associated Protein 2 (MAP2) Staining:

The brain sections were processed for immunohistochemical detection of neuronal cytoskeletal disruption. For antigen retrieval, the sections were heated in 10 mmol/L citrate buffer (pH 6.0) at 100° C. for 10 minutes. Endogenous peroxidase activity was blocked with 3% hydrogen peroxide for 10 minutes and after a second blocking with 5% normal goat serum, the sections were incubated with anti-microtubule-associated protein 2 (MAP2) antibody, diluted 1:1000 (mouse monoclonal antibody; Sigma, St. Louis, Mo., US) 1 h at room temperature. After rinsing, biotinylated goat anti-mouse immunoglobulin G (Vector Laboratories, Burlingame, Calif.) was added, and antibody detection was performed with the avidin-biotin complex method (Vector Laboratories), with 3,3'-diaminobenzidine (DAB) as the chromogen. Following the reaction with DAB, the slides were washed, dehydrated, and coverslipped.

Samples were analyzed with the aid of an image scanner (Nanozoomer Virtual Microscopy, Hamamatsu, Tokyo, Japan) and the ImageJ software (NIH, US). The MAP2 positive areas in the ipsilateral and contralateral hemispheres were measured. The ratio of the MAP2 positive areas was calculated as the MAP2 positive area of the ipsilateral hemisphere divided by the MAP2 positive area of the contralateral hemisphere. The ratio of the MAP2 positive area in the Sham group was considered by default as 1.0.

Doublecortin-Vascular Endothelial Growth Factor Double-Staining:

The sections were heated in 10 mmol/L citrate buffer (pH 6.0) at 100° C. for 10 minutes. Endogenous peroxidase activity was blocked with 3% hydrogen peroxide for 10 minutes and after a second blocking with 5% normal goat serum, the sections were incubated with anti-doublecortin (DCX) antibody, diluted 1:1000 (rabbit polyclonal antibody; Abcam, Cambridge, UK) and anti-vascular endothelial growth factor (VEGF) antibody, diluted 1:100 (mouse monoclonal antibody; Abcam, Cambridge, UK) overnight at 4° C. After rinsing, Alexa Fluor® goat anti-rabbit, diluted 1:1000 and Alexa Fluor® goat anti-mouse, diluted 1:1000 (Invitrogen Inc., Ghent, Belgium) were added and sections were incubated 1 h at room temperature. Mounting medium containing 4',6-diamidino-2-phenylindole (DAPI) for fluorescent studies was used (Vector Laboratories). Samples were analyzed with the aid of a microscope (Olympus Vanox AHBT3, Olympus), and the ImageJ software (NIH). The percentage of positively stained cells was quantified as a sum of positively stained either DCX or VEGF cells divided by the total number of DAPI positive cells expressed in percentage.

Detection of S1008 and Glial Fibrillary Acidic Protein (GFAP) in Blood Serum Samples: ELISAs for detecting the brain damage markers S100B protein (Catalog# CSB-E08066r, Cusabio Biotech Co., LTD, China), and glial fibrillary acidic protein (GFAP) (Catalog# E90068Ra, Uscn Life sciences Inc., China) in blood serum samples were performed according to the manufacturers' recommendations.

Statistical Analysis:

The analysis was conducted using the StatView software (Abacus Concepts, Inc., Berkeley, Calif., US). Statistical comparisons were performed using ANOVA followed by Fisher's PLSD, Scheffe's and Bonferroni/Dunn post-hoc tests with P<0.05 considered to indicate significance. All values are expressed as mean±SEM.

Example 2

Neuroprotective Effect of Estetrol in an Animal Model of Neonatal Hypoxic-Ischemic Encephalopathy After delivery, newborn rat pups were assigned to one of the following 4 groups: Sham group, Vehicle group, E4 5 mg/kg/per day group and E4 50 mg/kg/per day group. From day 4 to day 7 inclusive, rat pups were injected intraperitoneally either vehicle (Vehicle group) or E4 (5 mg/kg or 50 mg/kg in accordance to the group assignment) or not injected at all (Sham group). At day 7, 30 minutes after last injection, animals from Vehicle and E4 (5 mg/kg or 50 mg/kg) groups passed through surgery encompassing left common carotid artery double ligation and cut, followed by hypoxia produced by the inhalation of 11%-8% of oxygen balanced by nitrogen at decreased concentration for 20 minutes, followed by inhalation of 8% oxygen and 92% nitrogen at constant concentration for 35 minutes. The Sham group went through similar procedures without left common carotid artery ligation and hypoxia. All the manipulations were performed at 37° C. Rat pups recovered with their dams until being sacrificed at postnatal day 14.

Rat Pups Weight

Rat pups weight measurements were performed from day 4 to day 7 in order to determine the amount of vehicle and E4 necessary to inject, and from day 7 until up to day 14 in order to monitor the post-operative well-being of the rat pups.

At post-operative days 13 and 14 E4 5 mg/kg treated rat pups had significantly higher body weight than vehicle treated animals, whereas at other post-operative days sham operated group had significantly higher body weight than the other groups: days 8 (Sham vs. Vehicle and E4 5 mg/kg), 10 (Sham vs. E4 50 mg/kg), 12 (Sham vs. Vehicle), 13 (Sham vs. Vehicle) and 14 (Sham vs. Vehicle) (FIG. 1).

Brain Weight

Figure 2:
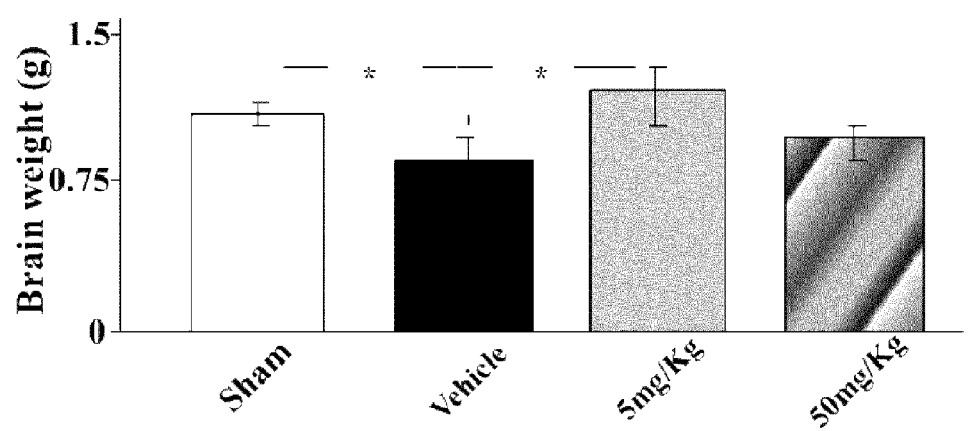
FIG. 2 Brain weights of rat pups. Brain weights of rat pups that were injected intraperitoneally from day 4 to day 7 including after delivery either by vehicle (saline solution) (Vehicle), 5 mg/kg E4 (5 mg/kg) or 50 mg/kg E4 (50 mg/kg) or not injected (Sham). Mean±SEM of brain weights upon sacrifice at day 14 after delivery of 7 rat pups from the Sham group, 11 rat pups of Vehicle groups, 7 rat pups from the E4 5 mg/kg group and 5 rat pups from the E4 50 mg/kg group are shown. Scalebar: 2 mm.

Measurement of brains weights revealed that they were significantly higher in E4 5 mg/kg and Sham operated groups than in the vehicle treated group (FIG. 2).

Figure 3:
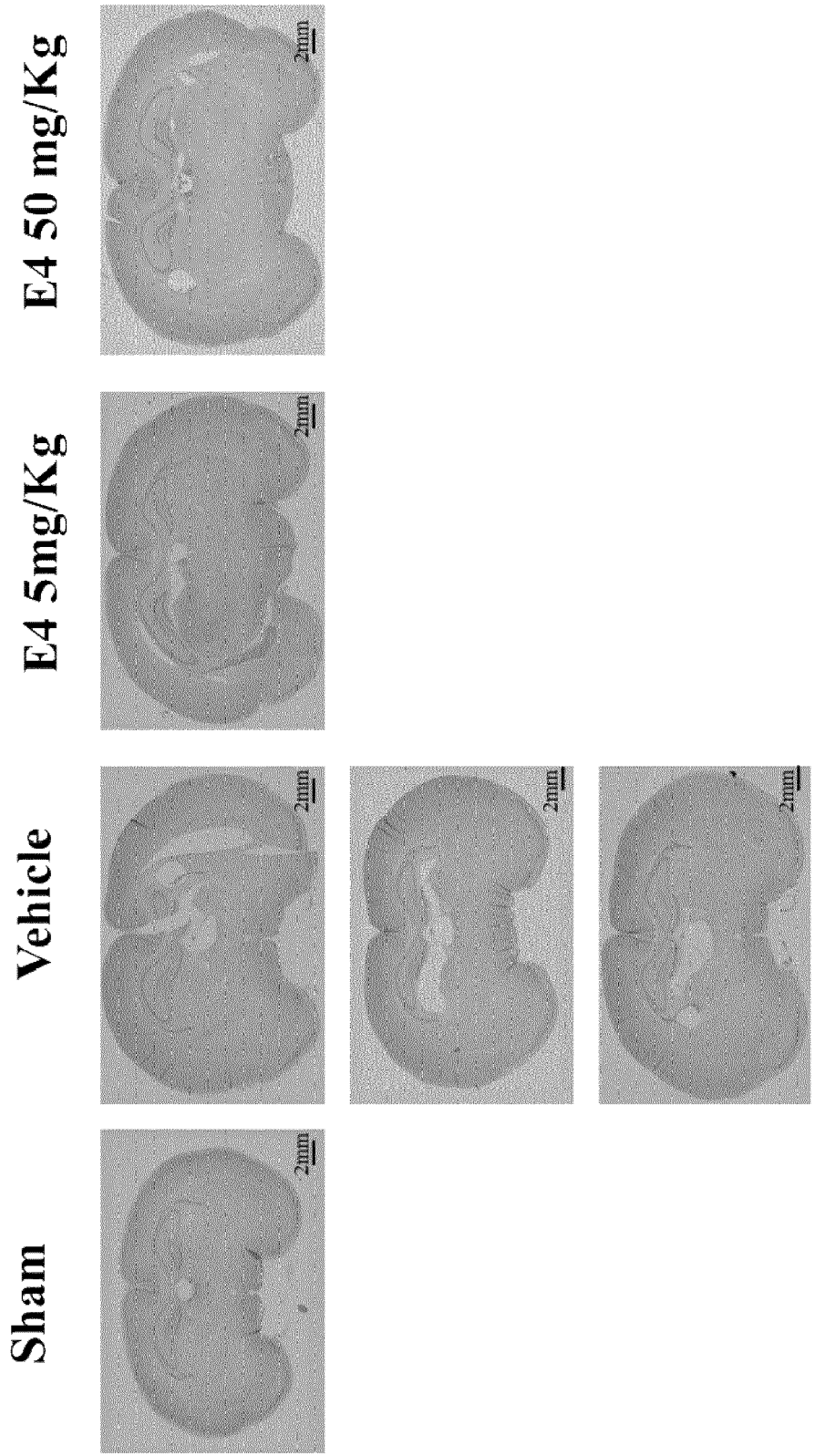
FIG. 3 Hematoxylin-Eosin staining of brain sections of the hippocampus region of rat pups. Brains of rat pups were removed upon sacrifice at day 14 after delivery and paraformaldehyde-fixed and paraffin-embedded samples were proceeded for sectioning at the hippocampus region and Hematoxylin-Eosin staining. Rat pups were either injected intraperitoneally from day 4 to day 7 including after delivery either by vehicle (saline solution) (Vehicle), 5 mg/kg E4 (E4 5 mg/kg) or 50 mg/kg E4 (E4 50 mg/kg) or not injected (Sham).

Hematoxylin-Eosin Staining (Histochemistry):

Only sections from the vehicle treated group showed visible disorganization of the hippocampus region ipsilateral to damage (left side), surrounded with infarct areas extended to the hippocampus region contralateral to damage (right side) (FIG. 3). These results show that E4, at both doses, has neuroprotective effect.

Figure 4:
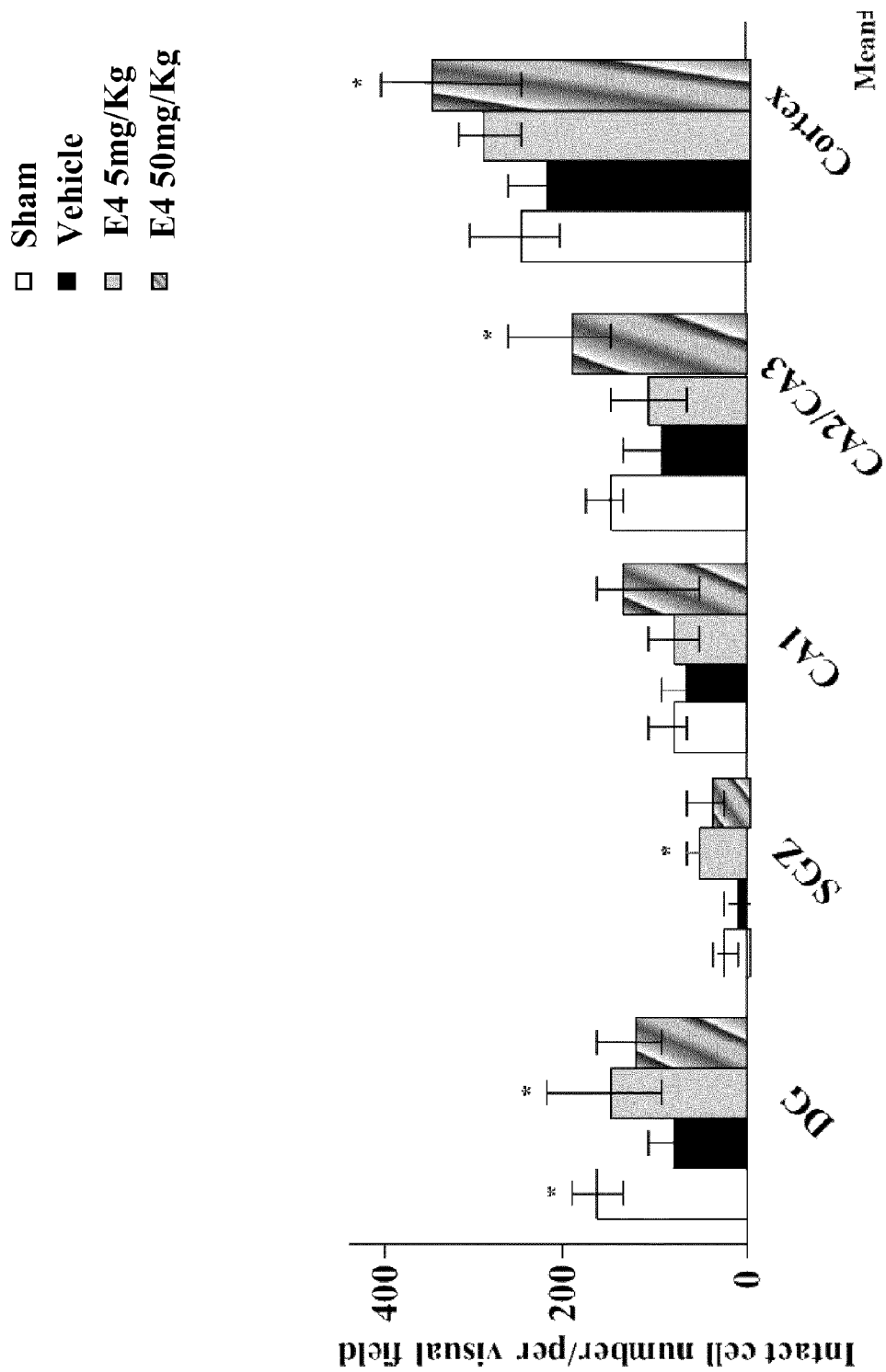
FIG. 4 Intact cell counting in Hematoxylin-Eosin-stained brain sections of rat pups. Intact cells were counted in hippocampus in dentate gyrus zone (DG), subgranular zone (SGZ) and cornu ammonis (CA1, CA2/CA3) and in cortex on Hematoxylin-Eosin-stained brain sections of rat pups. Intact cells were counted at magnification 400× in 3 fields of the respective brain area and the average is expressed as the intact cell number per visual field. Mean±SEM of intact cell number/visual field weights of 7 rat pups from the Sham group, 11 rat pups of Vehicle groups, 7 rat pups from the E4 5 mg/kg group and 5 rat pups from the E4 50 mg/kg group are shown.

Intact Cell Counting:

In DG region of hippocampus the number of intact cells per visual field was significantly higher in E4 5 mg/kg and Sham operated animal groups than in the Vehicle group (FIG. 4). In SGZ intact cell number was significantly higher in E4 5 mg/kg group alone in comparison with Sham and Vehicle groups, whereas in CA1 non-significant difference was detected among the study groups. In CA2/CA3 region of hippocampus E4 50 mg/kg group alone had a significantly higher number of intact cells than Vehicle treated and E4 5 mg/kg groups, whereas in cortex E4 50 mg/kg group had significantly higher number of intact cells compared to the Vehicle group alone. These results show that estetrol has neuroprotective effect.

Example 3

Neuroprotective Effect of Estetrol in an Animal Model of Neonatal Hypoxic-Ischemic Encephalopathy Newborn rat pups were assigned to one of the following 6 groups from postnatal day 4:

Sham group (n=24), Vehicle group (n=14), E4 1 mg/kg/per day group (n=11), E4 5 mg/kg/per day group (n=14), E4 10 mg/kg/per day group (n=14), or E4 50 mg/kg/per day group (n=19). From postnatal day 4, rat pups were intraperitoneally injected either vehicle (Vehicle group) or E4 (1, 5, 10, or 50 mg/kg/per day in accordance to the E4 group assignment) or neither vehicle nor E4 (Sham group). At day 7, 30 minutes after last injection, animals were anesthetized with isoflurane (induction, 3.0%; maintenance, 1.5%), and the rat pups from Vehicle and E4 groups passed through surgery encompassing left common carotid artery double ligation and cut. After the procedure, the pups were returned to their dams and were allowed to recover for 1 hour. The pups were then placed in the humidified hypoxic in vivo cabinet (CoyLab, Grass Lake, Mich., USA). Hypoxia was produced by the inhalation of 11%-8% of oxygen balanced by nitrogen at decreased concentration of oxygen for 20 minutes, followed by inhalation of 8% oxygen and 92% nitrogen at constant concentration for 35 minutes. All the manipulations were performed at 37° C. The Sham group went through similar procedures without left common carotid artery ligation followed by hypoxia nor injection. Rat pups recovered with their dams and reared normally until being sacrificed at postnatal day 14.

Rectal Temperature:

Rectal temperatures were not significantly different between the study groups, indicating that estetrol pre-treatment did not affect the body temperature (data not shown).

Body Weight

Figure 5:
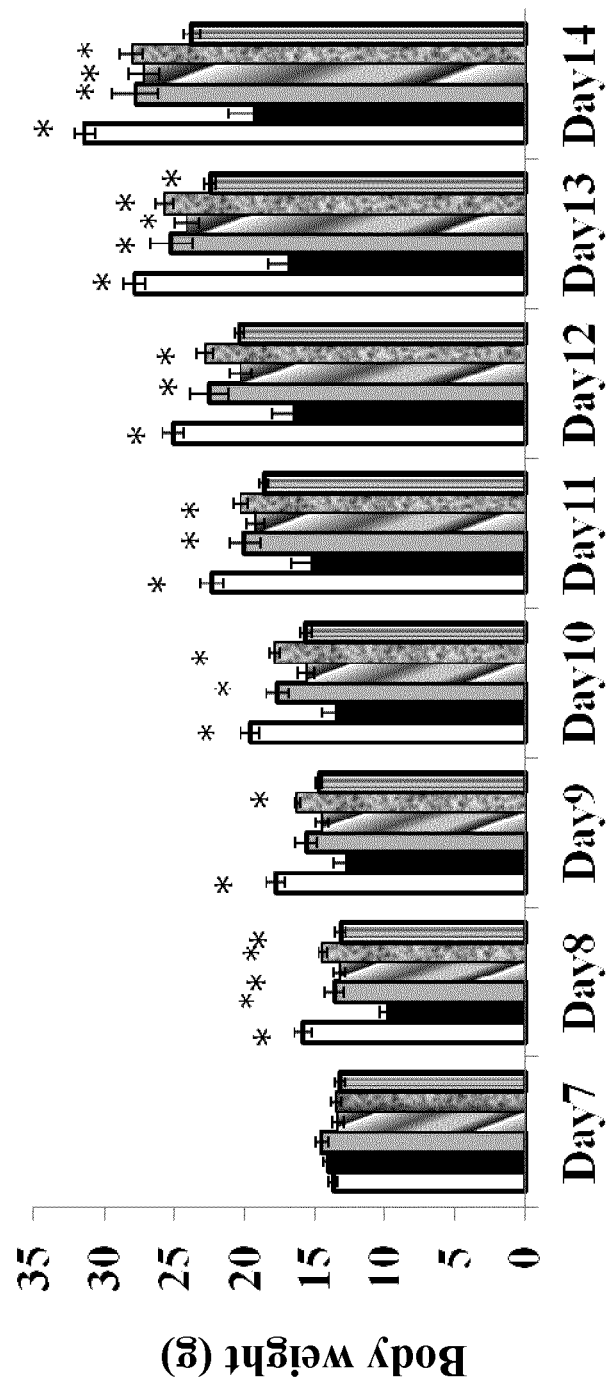
FIG. 5 Post-operative body weight of rat pups that were pre-treated with estetrol. At each indicated post-natal day (X-axis), the 6 bars represent, from left to right, post-operative body weight (in g) of rat pups that were, respectively, not injected with vehicle or E4 (Sham group, n=24), injected intraperitoneally from postnatal day 4 to day 7 inclusive with vehicle (Vehicle group, n=14), injected intraperitoneally from postnatal day 4 to day 7 inclusive with 1 mg/kg E4 (n=11), injected intraperitoneally from postnatal day 4 to day 7 inclusive with 5 mg/kg E4 (n=14), injected intraperitoneally from postnatal day 4 to day 7 inclusive with 10 mg/kg E4 n=(14), or injected intraperitoneally from postnatal day 4 to day 7 inclusive with 50 mg/kg E4 (n=19). At postnatal day 7, 30 minutes after last injection, rat pups underwent hypoxic-ischemic insult. Sham animals went through similar procedures without hypoxic-ischemic insult. Measurements are expressed as mean±SEM.

To monitor the post-operative well-being of the rat pups due to the performed manipulations and estetrol pre-treatment, the body weight was monitored from postnatal day 7 to day 14 inclusive. FIG. 5 shows that at postnatal days 8 and 13 sham operated and estetrol pre-treated rat pups had significantly higher post-operative body weight than the vehicle pre-treated animals. Furthermore, at postnatal day 9 sham operated and 10 mg/kg estetrol pre-treated animals had significantly higher body weight than the vehicle group, whereas at postnatal days 10, 11 and 12 sham operated, 1 mg/kg and 10 mg/kg estetrol pre-treated rat pups showed significantly higher body weight than the vehicle group. At postnatal day 14 sham and 1 mg/kg, 5 mg/kg, and 10 mg/kg estetrol pre-treated animals had significantly higher body weight than the vehicle group alone. However, at postnatal days 8, 9, 10, 12 sham operated animals body weight was significantly higher than the 5 mg/kg and 50 mg/kg estetrol pre-treated groups, whereas at postnatal days 11, 13, 14 sham operated animals had significantly higher body weight than the 50 mg/kg estetrol pre-treated group alone.

Brain Weight

Figure 6:
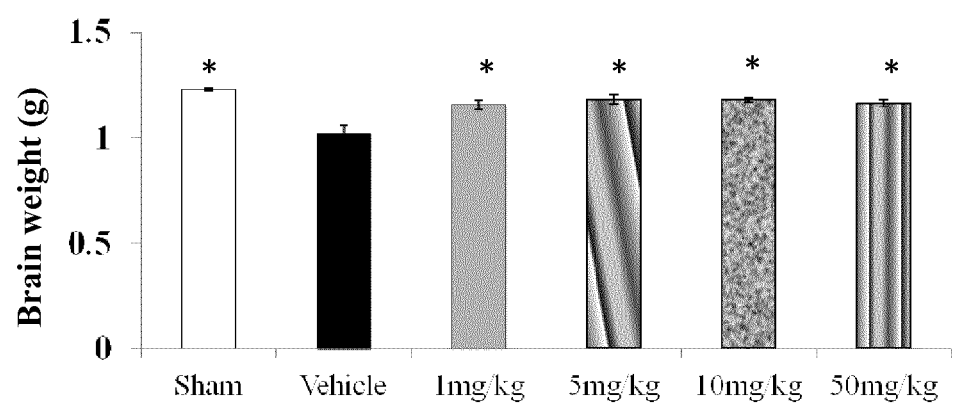
FIG. 6 Brain weight of rat pups that were pre-treated with estetrol. Brain weight (in g) of rat pups that were not injected with vehicle or with E4 (Sham group, n=24), or injected intraperitoneally from postnatal day 4 to day 7 inclusive with vehicle (Vehicle group, n=14), 1 mg/kg E4 (n=11), 5 mg/kg E4 (n=14), 10 mg/kg E4 (n=14) or 50 mg/kg E4 (n=19). At postnatal day 7, 30 minutes after last injection, rat pups underwent hypoxic-ischemic insult. Sham animals went through similar procedures without hypoxic-ischemic insult. Measurements are expressed as mean±SEM.

To assess possible brain damage, measurement of the rat pups brains was performed. FIG. 6 demonstrates that the brain weight was significantly higher in the Sham group (1.225±0.006 g), and the 1 mg/kg E4 (1.155±0.022 g), 5 mg/kg E4 (1.181±0.023 g), 10 mg/kg E4 (1.179±0.012 g), and 50 mg/kg E4 (1.163±0.016 g) pre-treated groups than in the vehicle group (1.016±0.042 g).

Figure 7:
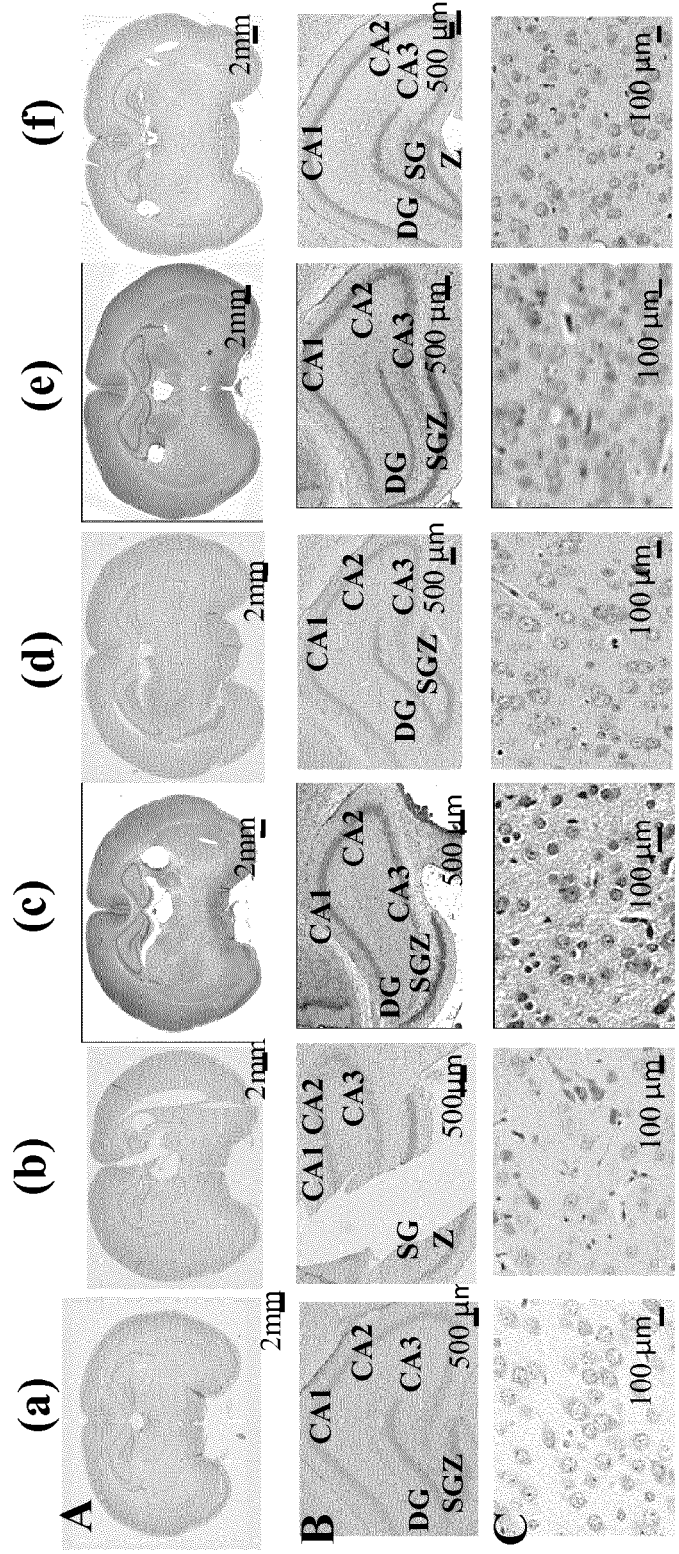
FIG. 7 Hematoxylin-eosin staining of coronal brain sections and intact cells counting in rat pups that were pre-treated with estetrol. Rat pups were (a) not injected with vehicle or with E4 (Sham group, n=14), or injected intraperitoneally from postnatal day 4 to day 7 inclusive with (b) vehicle (Vehicle group, n=16), (c) 1 mg/kg E4 (n=10), (d) 5 mg/kg E4 (n=13), (e) 10 mg/kg E4 n=(10) or (f) 50 mg/kg E4 (n=14). At postnatal day 7, 30 minutes after last injection, rat pups underwent hypoxic-ischemic insult. Sham animals went through similar procedures without hypoxic-ischemic insult. Brains were removed upon sacrifice at postnatal day 14 and paraformaldehyde-fixed and paraffin-embedded brain samples were coronally sectioned at the hippocampus region. Hematoxylin-eosin staining of (A) brain coronal sections (scale bar: 2 mm), (B) hippocampus region (scale bar: 500 μm), and (C) cortex (scale bar: 100 μm) of study groups are shown. (D) Intact cells were counted in different regions of the hippocampus: dentate gyrus (DG), subgranular zone (SGZ), and cornu ammonis (CA1, CA2/CA3), and in the cortex on hematoxylin-eosin-stained coronal brain sections of rat pups. Intact cells were counted at magnification 400× in 3 fields of the respective brain area and the average is expressed as the intact cell number per visual field. For each indicated brain region (DG, SGZ, CA1, CA2/3, Cortex on X-axis), the 6 bars represent, from left to right, intact cell number per visual field of rat pups from, respectively, Sham group, Vehicle group, rat pups treated with 1 mg/kg E4, rat pups treated with 5 mg/kg E4, rat pups treated with 10 mg/kg E4 or rat pups treated with 50 mg/kg E4. All measurements are shown as mean±SEM.
Figure 7:
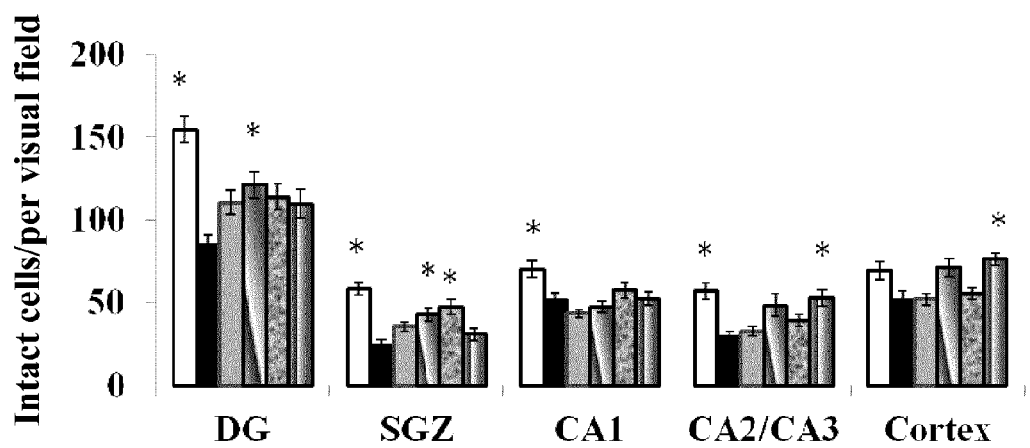

Hematoxylin-Eosin Staining and Intact Cell Counting:

The brain sections from vehicle pre-treated rat pups showed visible disorganization and damage of the hippocampus region ipsilateral to damage (left side) extended to the cortex (FIG. 7 A-C).

In the DG region of the hippocampus the number of intact cells per visual field was significantly higher in sham operated animals (154.5±7.942) (FIG. 7B(a)) and animals injected with 5 mg/kg E4 (121.0±8.098) (FIG. 7B(d)) than in the vehicle group (84.563±5.954) (FIG. 7B(b)) (FIG. 7D). Furthermore, SGZ intact cell number was significantly higher in the Sham group (58.357±3.653) (FIG. 7B(a)), the 5 mg/kg E4 group (42.846±3.884) (FIG. 7B(d)) and the 10 mg/kg E4 group (47.6±4.672) (FIG. 7B(e)) than in the vehicle group (23.875±3.363) (FIG. 7B(b)) (FIG. 7D), whereas in the same region the sham group showed a significantly higher number of intact cells than the 1 mg/kg E4 group (35.6±2.75) (FIG. 7B(c)) and the 50 mg/kg E4 group (30.714±3.615) (FIG. 7B(f)) (FIG. 7D). In CA1 region significant difference was detected among the sham group (70.714±4.819) (FIG. 7B(a)), and the 1 mg/kg E4 (43.2±2.435) (FIG. 7B(c)) and 10 mg/kg E4 (57.4±4.566) (FIG. 7B(e)) groups, whereas other groups did not show significant difference (FIG. 7D). In CA2/CA3 region of hippocampus sham (56.929±4.859) (FIG. 7B(a)) and 50 mg/kg E4 (53.0±4.7) (FIG. 7B(f)) groups had a significantly higher number of intact cells than the vehicle group (29±3.543) (FIG. 7B(b)), whereas the sham group alone had a significantly higher number of intact cells than the 1 mg/kg E4 group (32.8±2.808) (FIG. 7B(c)) (FIG. 7D). In the cortex the 50 mg/kg E4 group (76.286±3.962) (FIG. 7C(f)) showed a significantly higher number of intact cells than the vehicle group alone (51.938±5.304) (FIG. 7C(b)) (FIG. 7D).

Figure 8:
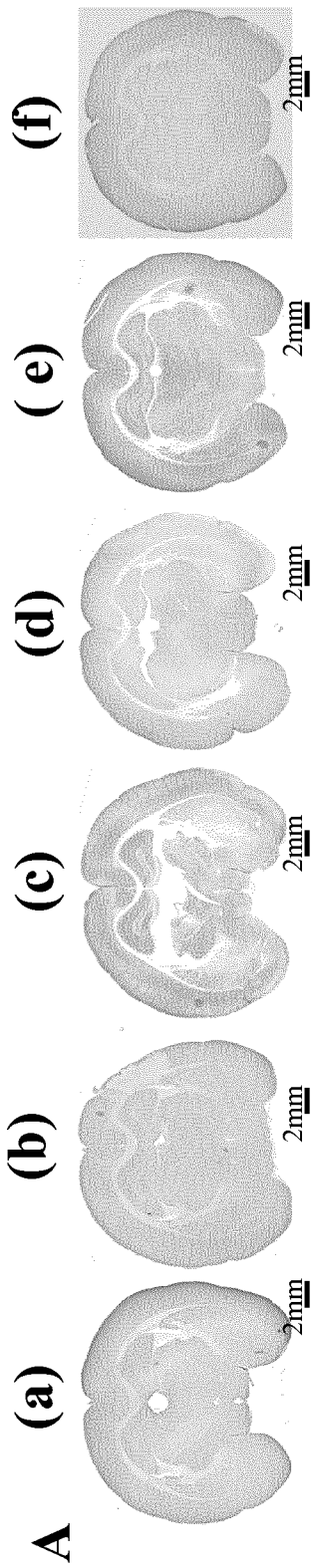
FIG. 8 Microtubule-associated protein 2 (MAP2) staining of brain coronal sections in rat pups that were pre-treated with estetrol. Rat pups were (a) not injected with vehicle or with E4 (Sham group), or injected intraperitoneally from postnatal day 4 to day 7 inclusive with (b) vehicle (Vehicle group), (c) 1 mg/kg E4, (d) 5 mg/kg E4, (e) 10 mg/k gE4 or (f) 50 mg/kg E4. At postnatal day 7, 30 minutes after last injection, rat pups underwent hypoxic-ischemic insult. Sham animals went through similar procedures without hypoxic-ischemic insult. Brains were removed upon sacrifice at postnatal day 14 and paraformaldehyde-fixed and paraffin-embedded brain samples were coronally sectioned at the hippocampus region. The sections were processed for detection of neuronal cytoskeletal disruption through immunohistological staining with anti-MAP2 antibody. (A) MAP2 staining of brain coronal sections (scale bar: 2 mm) is shown. (B) The ratio of the MAP2 positive areas was calculated as the MAP2 positive area of the ipsilateral hemisphere divided by the MAP2 positive area of the contralateral hemisphere. 10 samples from each study group were analyzed. The ratio of the MAP2 positive area in the Sham group was considered by default as 1.
Figure 8:
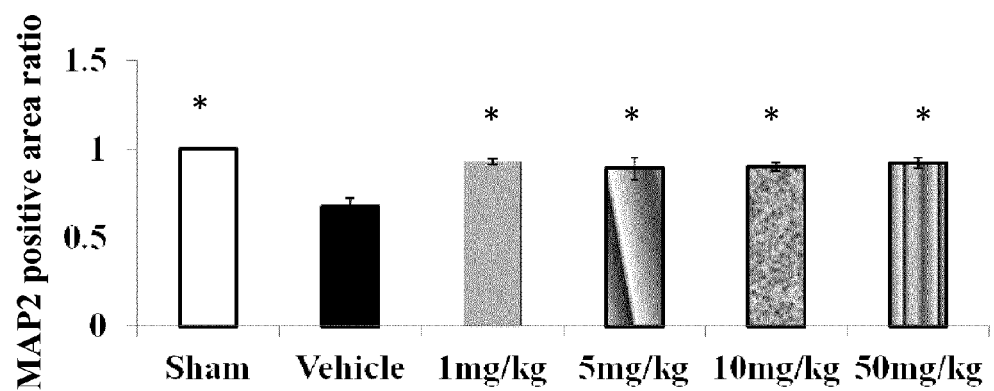

MAP2 Staining:

Loss of ipsilateral MAP2 staining as determined after hypoxia-ischemia (HI) at postnatal day 14 was used as a marker of early grey matter area loss. The area with intact neurons displayed staining with MAP2, whereas the infarcted area showed a loss of MAP2 staining. In particular, in the vehicle group there was a loss of MAP2 staining in the hippocampal area of the ipsilateral to damage hemisphere extended to the cortex (FIG. 8A(b)). Quantification of the ratio of the MAP2-positive areas revealed that after estetrol pre-treatment (FIG. 8B) the ratio of MAP2-positive area was significantly higher in sham operated animals (by default 1.0) (FIG. 8A(a)), and estetrol pre-treated groups (1 mg/kg E4 (0.929±0.019) (FIG. 8A(c)), 5 mg/kg E4 0.889±0.063 (FIG. 8A(d)), 10 mg·kg E4 (0.898±0.022) (FIG. 8A(e)), 50 mg/kg E4 (0.922±0.031) (FIG. 8A(f))) than in the vehicle group (0.675±0.046) (FIG. 8A(b)).

Figure 9:
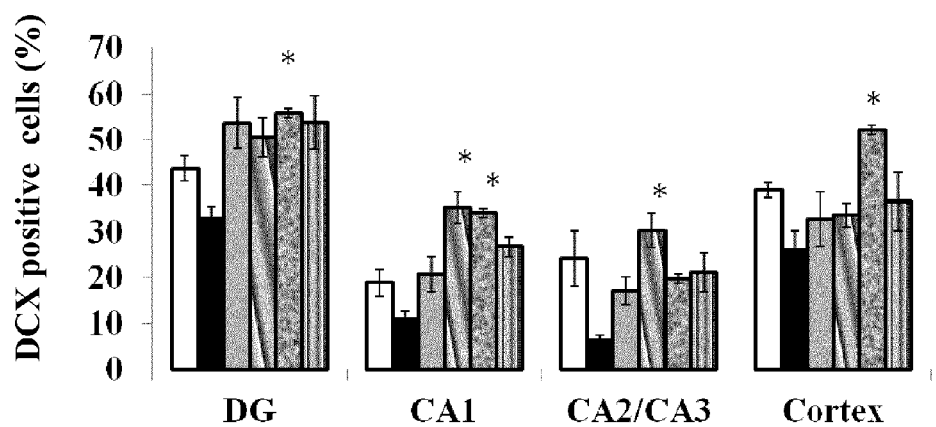
FIG. 9 Doublecortine (DCX) and Vascular Endothelial Growth Factor (VEGF) staining in hippocampus and cortex of rat pups pre-treated with estetrol. Rat pups were not injected with vehicle or with E4 (Sham group), or injected intraperitoneally from postnatal day 4 to day 7 inclusive with vehicle (Vehicle group), 1 mg/kg E4, 5 mg/kg E4, 10 mg/kg E4 or 50 mg/kg E4. At postnatal day 7, 30 minutes after last injection, rat pups underwent hypoxic-ischemic insult. Sham animals went through similar procedures without hypoxic-ischemic insult. Brains were removed upon sacrifice at postnatal day 14 and paraformaldehyde-fixed and paraffin-embedded brain samples were coronally sectioned at the hippocampus region. The sections were double-stained with anti-DCX antibody and anti-VEGF antibody. The percentage of DCX (A) and VEGF (B) positive cells was quantified as the sum of either DCX or VEGF positively stained cells divided by the total number of DAPI positive cells. Quantifications were made in different regions of the hippocampus ((dentate gyrus (DG), cornu ammonis1 (CA1), cornu ammonis 2/3 (CA2/CA3)), and in the cortex. 10 samples were analyzed in the Sham, 1 mg/kg E4, 5 mg/kg E4, 10 mg/kg E4, 50 mg/kg E4 groups and compared with 12 samples from the Vehicle group. For each indicated brain region (DG, CA1, CA2/3, Cortex on X-axis), the 6 bars represent, from left to right, percentage of DCX (A) or VEGF (B) positive cells in, respectively, Sham group, Vehicle group, 1 mg/kg E4 group, 5 mg/kg E4 group, 10 mg/kg E4 group, or 50 mg/kg E4 group. All measurements are shown as mean±SEM.
Figure 9:
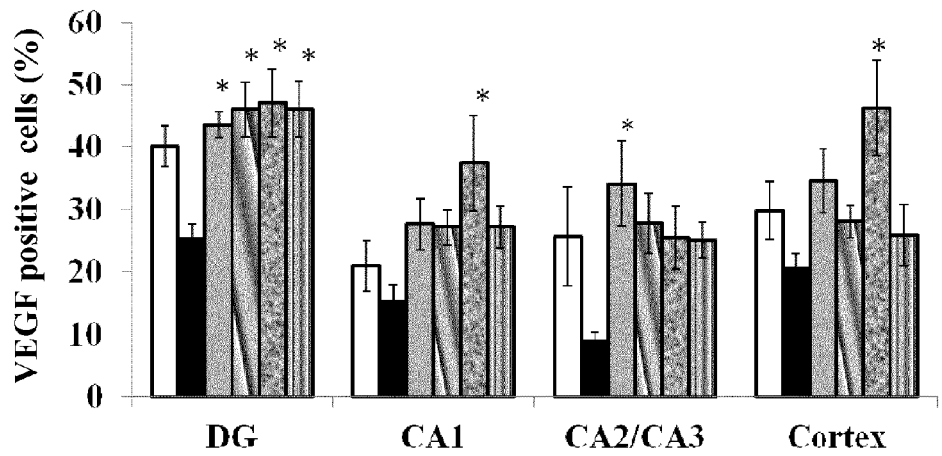

Doublecortine-Vascular Endothelial Growth Factor Double-Staining:

Expression of DCX and VEGF at postnatal day 14 was used as a marker of neuro- and vasculogenesis, respectively. Estetrol pre-treatment resulted in the DG region of the hippocampus in a significantly higher percentage of DCX positively stained cells in animals pre-treated with 10 mg/kg E4 (55.8±5.658%) than in the vehicle group (32.833±2.625%) (FIG. 9A), whereas in the same region the percentage of VEGF positively stained cells was significantly higher in the group pre-treated with 1 mg/kg E4 (43.5±2.083%), 5 mg/kg E4 (46.0±4.361%), 10 mg/kg E4 (47.0±5.362%), and 50 mg/kg E4 (46.0±4.465%) than in the vehicle group (25.333±2.271%) (FIG. 9B). Furthermore, in the CA1 region the percentage of DCX positively stained cells was significantly higher in the groups 5 mg/kg E4 (35.2±3.309%), and 10 mg/kg E4 (34.1±6.664%) than in the vehicle group (11±1.518%) (FIG. 9A), whereas the percentage of VEGF positively stained cells was significantly higher in the 10 mg/kg E4 group (37.4±7.645%) alone (FIG. 9B). In the CA2/CA3 region the percentage of DCX positively stained cells was significantly higher in the 5 mg/kg E4 group (30.3±3.7%) than in the vehicle group (6.417±1.033%), whereas the percentage of VEGF positively stained cells reached significant difference only in 1 mg/kg E4 group (34.1±6.855%) (FIG. 9B). In the cortex the percentage of DCX and VEGF positively stained cells was significantly higher in the group 10 mg/kg E4 (52.1±7.762% and 46.2±7.646%, respectively) than in the vehicle group alone (26.0±4.156% and 20.5±2.414%, respectively) (FIG. 9A-B, respectively).

Figure 10:
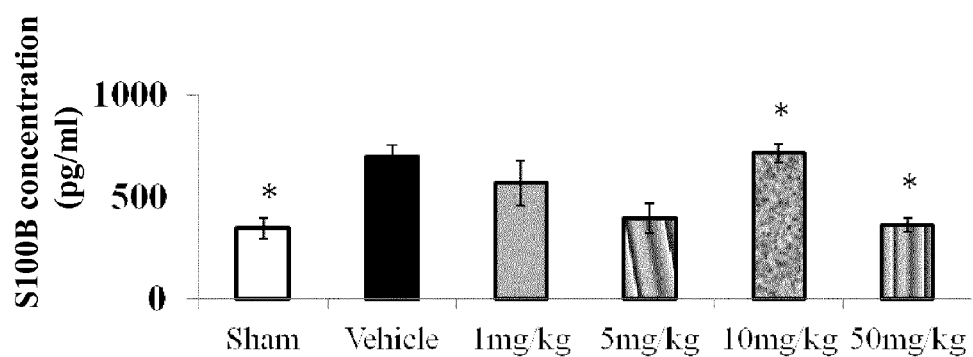
FIG. 10 S100B and Glial Fibrillary Acidic Protein (GFAP) expression in blood serum of rat pups that were pre-treated with estetrol. Rat pups were not injected with vehicle or with E4 (Sham group, n=20 and n=21 for S100B and GFAP, respectively), or injected intraperitoneally from postnatal day 4 to day 7 inclusive with vehicle (Vehicle group, n=13 and n=15 for S100B and GFAP, respectively), 1 mg/kg E4 (n=10 and n=11 for S100B and GFAP, respectively), 5 mg/kg E4 (n=11 and n=11 for S100B and GFAP, respectively), 10 mg/kg E4 (n=13 and n=10 for S100B and GFAP, respectively) or 50 mg/kg E4 (n=19 and n=18 for S100B and GFAP, respectively). At postnatal day 7, 30 minutes after last injection, rat pups underwent hypoxic-ischemic insult. Sham animals went through similar procedures without hypoxic-ischemic insult. Blood samples were drawn upon sacrifice at postnatal day 14. ELISA for S100B and GFAP proteins were performed to examine the concentration of S100B (A) GFAP (B) in the blood sera. All measurements are shown as mean±SEM.
Figure 10:
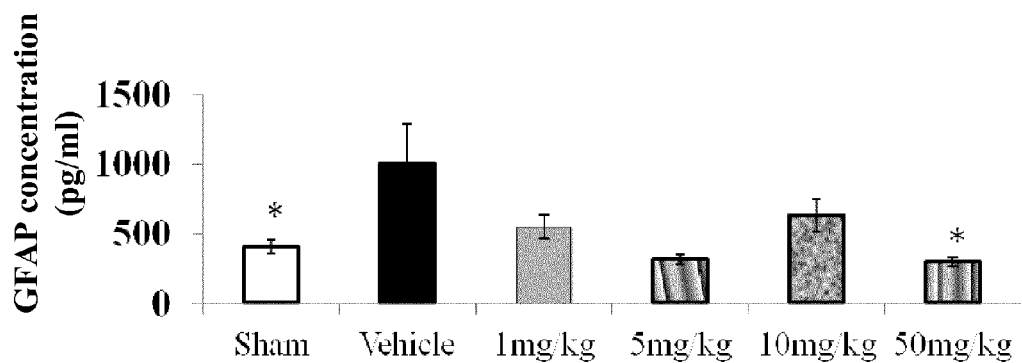

Blood Serum S100B and Glial Fibrillary Acidic Protein (GFAP):

S100B and glial fibrillary acidic protein (GFAP) were used as markers of brain damage. Their concentration was measured in blood sera by ELISA for S100B and GFAP proteins. As shown in FIG. 10A, after estetrol pre-treatment the concentration of S100B was significantly lower in sham operated animals (344.614±50.328 pg/ml), and the 50 mg/kg E4 group (361±32.914 pg/ml) than in vehicle pre-treated animals (698.925±57.342 pg/ml), although in the 10 mg/kg E4 group S100B concentration was significantly higher than in the sham, 5 mg/kg E4, and 50 mg/kg E4 groups.

FIG. 10B shows that significantly decreased concentration of GFAP in sham operated animals (407,567±49.258 pg/ml), and animals pre-treated with 50 mg/kg E4 (300.388±31.232 pg/ml) were observed than in the vehicle group (1003.926±288.345 pg/ml).

Conclusion:

The present results demonstrate that estetrol has a neuroprotective dose-dependent effect in the hippocampal formation and cortex in an animal model of HIE. Also in accordance to the present results, estetrol pre-treatment decreases early gray matter loss and promotes neuro- and vasculogenesis. Moreover, estetrol pre-treatment has no adverse effects on body weight, brain weight or body temperature.

Example 4

Therapeutic Effect of Estetrol in an Animal Model of Neonatal Hypoxic-Ischemic Encephalopathy To study the therapeutic effect of estetrol, newborn rat pups were assigned to one of the following 6 groups at postnatal day 7: sham group (n=29), vehicle group (n=20), 1 mg/kg E4 group (n=16), 5 mg/kg E4 group (n=19), 10 mg/kg day E4 (n=17) and 50 mg/kg day E4 group (n=15). At postnatal day 7 animals were anesthetized with isoflurane (induction, 3.0%; maintenance, 1.5%), and the rat pups from vehicle and E4 groups passed through surgery encompassing left common carotid artery double ligation and cut. After surgery, the pups were returned to their dams and allowed to recover for 1 hour. The pups were then placed in a humidified hypoxic in vivo cabinet (CoyLab). Hypoxia was produced by the inhalation of 11%-8% of oxygen balanced by nitrogen at decreased concentration of oxygen for 20 minutes, followed by inhalation of 8% oxygen and 92% nitrogen at constant concentration for 35 minutes. All the manipulations were performed at 37° C.

Upon retrieval from the hypoxia chamber the rat pups were injected intraperitoneally either by vehicle (vehicle group) or by E4 (1 mg/kg, 5 mg/kg, 10 mg/kg or 50 mg/kg) in accordance to the group assignment. The animals from the sham group went through similar procedures but proceeded neither left common carotid artery ligation and cut followed by hypoxia nor vehicle or estetrol administration. Rat pups recovered with their dams until being sacrificed at postnatal day 14.

Rectal Temperature:

Rectal temperatures were not significantly different between the study groups, indicating that estetrol treatment did not affect the body temperature (data not shown).

Body Weight

Figure 11:
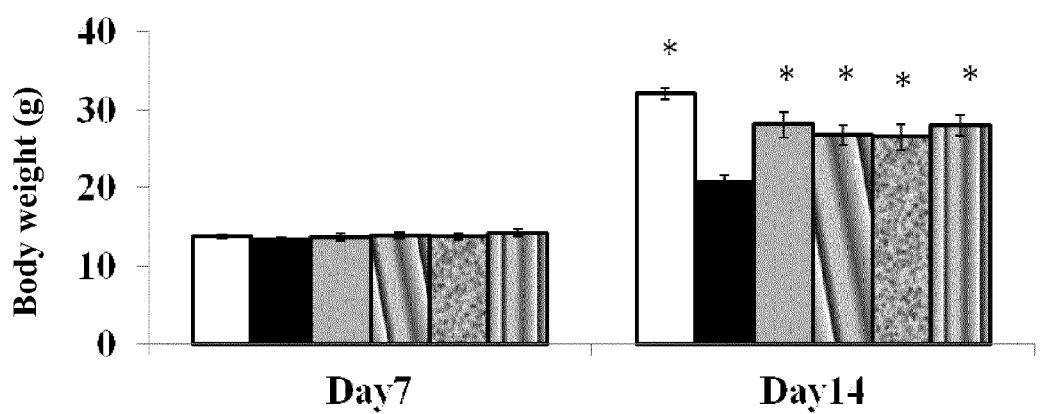
FIG. 11 Post-operative body weight of rat pups that were treated with estetrol. At postnatal day 7, rat pups underwent hypoxic-ischemic insult. Upon retrieval from hypoxia, the rat pups were injected intraperitoneally by a single dose of vehicle (Vehicle group, n=20), 1 mg/kg E4 (n=16), 5 mg/kg E4 n=19), 10 mg/kg E4 (n=17) or 50 mg/kg E4 (n=15). Sham animals underwent similar procedures without hypoxic-ischemic insult and they were not injected with vehicle nor E4 (Sham group, n=29). At each indicated post-natal day (X-axis), the 6 bars represent, from left to right, post-operative body weight (in g) of the rat pups from, respectively, Sham group, Vehicle group, 1 mg/kg E4 group, 5 mg/kg E4 group, 10 mg/kg E4 group, or 50 mg/kg E4 group. Measurements are expressed as mean±SEM.

To evaluate the post-operative well-being of rat pups due to the performed manipulations and estetrol treatment, the post-operative body weight was measured at postnatal days 7 and 14. FIG. 11 shows that at postnatal day 14 sham operated animals, and animals from the 1 mg/kg E4, 5 mg/kg E4, 10 mg/kg E4, and 50 mg/kg E4 groups had significantly higher body weight than the vehicle group. Sham operated animals showed significantly higher body weight than the 5 mg/kg E4 treated group.

Brain Weight

Figure 12:
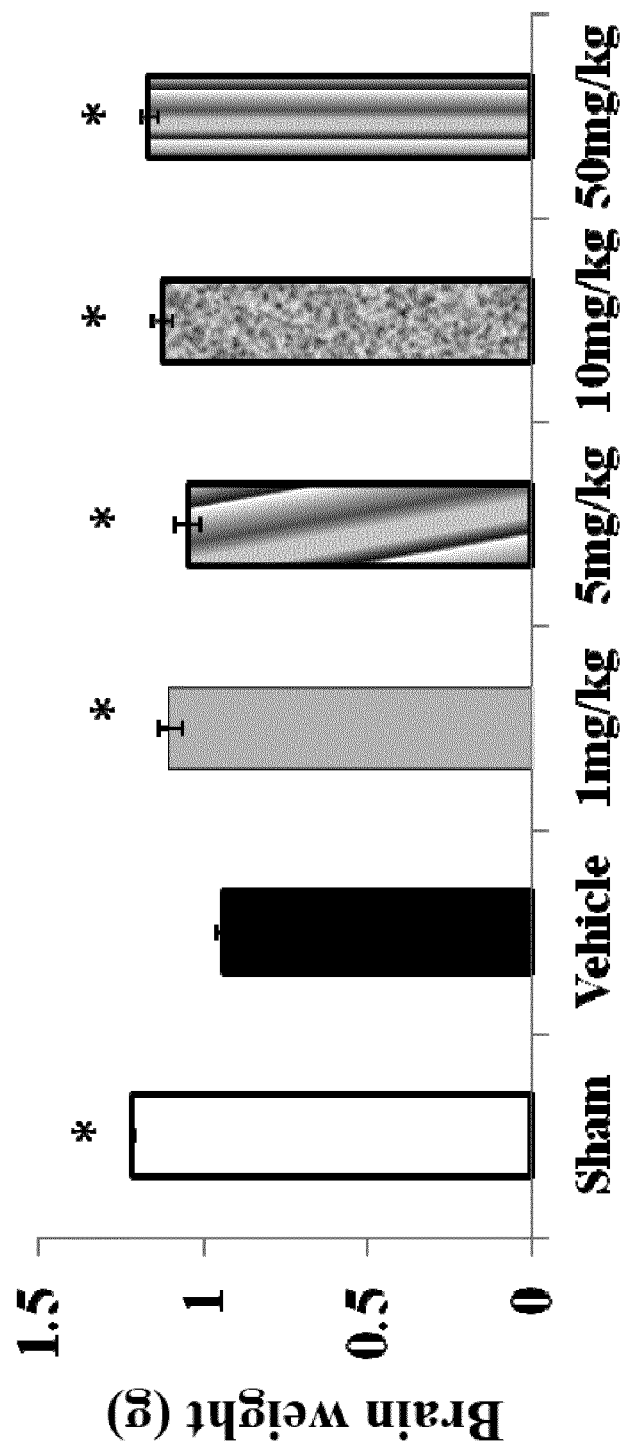
FIG. 12 Brain weight of rat pups that were treated with estetrol. At postnatal day 7, rat pups underwent hypoxic-ischemic insult. Upon retrieval from hypoxia, the rat pups were injected intraperitoneally by a single dose of vehicle (Vehicle group, n=20), 1 mg/kg E4 (n=16), 5 mg/kg E4 n=19), 10 mg/kg E4 (n=17) or 50 mg/kg E4 (n=15). Sham animals underwent similar procedures without hypoxic-ischemic insult and they were not injected with vehicle nor E4 (Sham group, n=29). Brain weight (in g) of the rat pups is shown. Measurements are expressed as mean±SEM.

FIG. 12 demonstrates that the brain weight was significantly higher in sham operated animals (1.214±0.007 g), and the 1 mg/kg E4 (1.099±0.037 g), 5 mg/kg E4 (1.06±0.035 g), 10 mg/kg E4 (1.12±0.33 g), and 50 mg/kg E4 (1.163±0.025 g) groups than in the vehicle group (0.937±0.022 g). Sham operated animals showed significantly higher brain weight than the 5 mg/kg E4 group. This pattern of results is the same as in example 3.

Figure 13:
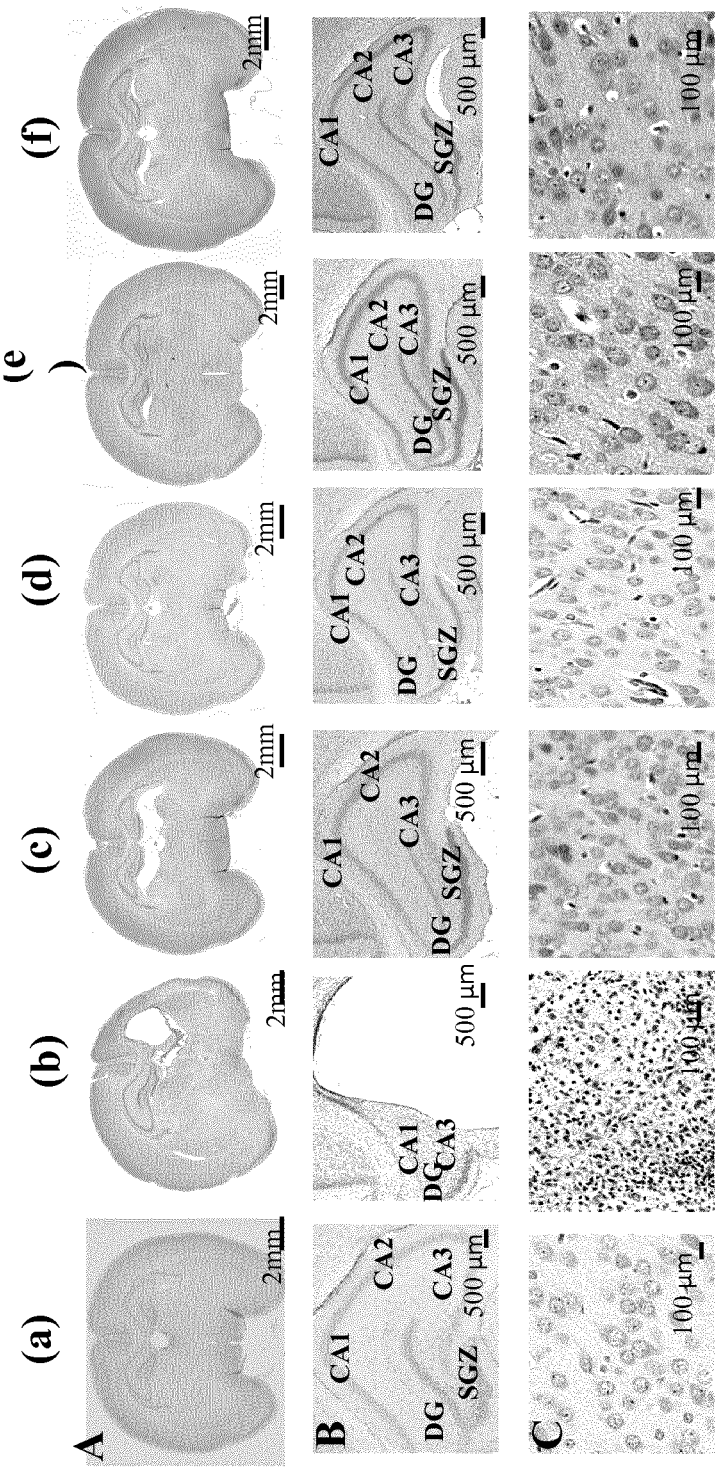
FIG. 13 Hematoxylin-eosin staining of coronal brain sections and intact cells counting in rat pups that were treated with estetrol. At postnatal day 7, rat pups underwent hypoxic-ischemic insult. Upon retrieval from hypoxia, the rat pups were injected intraperitoneally by a single dose of (b) vehicle (Vehicle group, n=10), (c) 1 mg/kg E4 (n=10), (d) 5 mg/kg E4 (n=10), (e) 10 mg/kg E4 (n=10) or (f) 50 mg/kg E4 (n=10). Sham animals (a) underwent similar procedures without hypoxic-ischemic insult and were not injected with vehicle nor E4 (Sham group, n=10). Brains were removed upon sacrifice at postnatal day 14 and paraformaldehyde-fixed and paraffin-embedded samples were proceeded for coronal sectioning at the hippocampus region followed by hematoxylin-eosin staining. Hematoxylin-eosin staining of (A) brain coronal sections (scale bar: 2 mm), (B) hippocampal region (scale bar: 500 μm), and (C) cortex (scale bar: 100 μm) are shown. (D) Intact cells were counted in different regions of the hippocampus: dentate gyrus (DG), subgranular zone (SGZ), and cornu ammonis (CA1, CA2/CA3), and in the cortex on hematoxylin-eosin-stained coronal brain sections. Intact cells were counted at magnification 400× in 3 fields of the respective brain area and the average is expressed as the intact cell number per visual field. For each indicated brain region (DG, SGZ, CA1, CA2/3, Cortex on X-axis), the 6 bars represent, from left to right, intact cell number per visual field of rat pups from, respectively, Sham group, Vehicle group, rat pups treated with 1 mg/kg E4, rat pups treated with 5 mg/kg E4, rat pups treated with 10 mg/kg E4, or rat pups treated with 50 mg/kg E4. All measurements are shown as mean±SEM.
Figure 13:
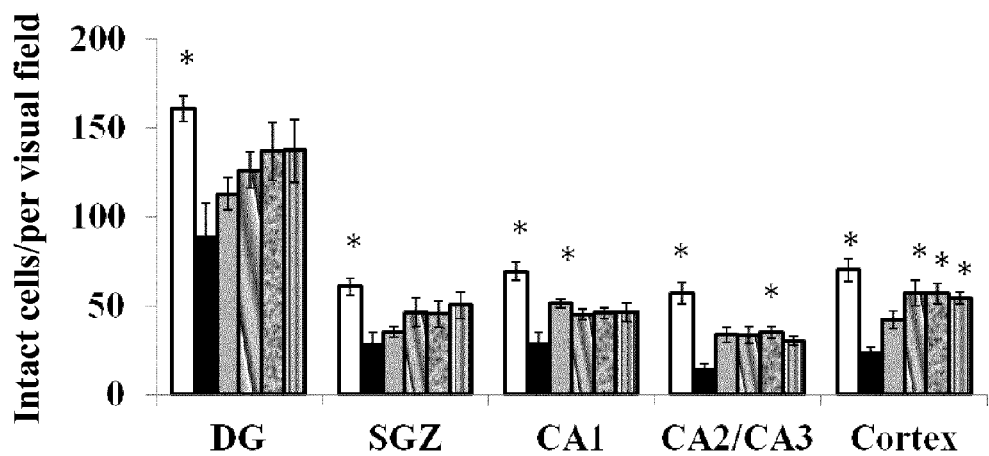

Hematoxylin-Eosin Staining and Intact Cell Counting:

In the DG and SGZ regions of the hippocampus the number of intact cells per visual field was significantly higher in sham operated animals (FIG. 13B(a)) than in animals from the vehicle group (FIG. 13B(b)) (160.8±7.074 vs. 88.2±19.477, and 60.8±4.635 vs. 28.3±6.73, respectively) (FIG. 13D). In the CA1 region intact cells number was significantly higher in the sham group (69.4±5.256) (FIG. 13B(a)) and the 1 mg/kg E4 group (51.5±2.5) (FIG. 13B(c)) than in the vehicle group (28.4±6.997) (FIG. 13B(b)), and in the sham group than in the 5 mg/kg E4 group (45.3±2.989) (FIG. 13B(d)), the 10 mg/kg E4 group (46.0±3.19) (FIG. 13B(e)), and the 50 mg/kg E4 group (46.6±5.336) (FIG. 13B(f)) (FIG. 13D). In the CA2/CA3 region of the hippocampus sham operated animals (57.1±6.192) (FIG. 13B(a)) and animals treated with 10 mg/kg E4 (35.2±3.169) (FIG. 13B(e)) had a significantly higher number of intact cells than the vehicle group (13.8±3.018), whereas the sham group had a significantly higher number of intact cells than the 1 mg/kg E4 (33.9±4.306), 5 mg/kg E4 (33.8±4.704), 10 mg/kg E4 (35.2±3.169), and 50 mg/kg E4 (30.5±2.527) groups (FIG. 13D). In the cortex sham operated animals (70.1±6.165) (FIG. 13C(a)) and animals treated with 5 mg/kg E4 (57.1±7.012) (FIG. 13C(d)), 10 mg/kg E4 (56.9±5.958) (FIG. 13C(e) and 50 mg/kg E4 (54.5±3.403) (FIG. 13C(f)) showed significantly higher number of intact cells than the vehicle group (23.2±3.872) (FIG. 13C(b)), whereas the sham group had a significantly higher number of intact cells than the 1 mg/kg E4 group (42.4±4.865) (FIG. 13C(c)) (FIG. 13D).

Figure 14:
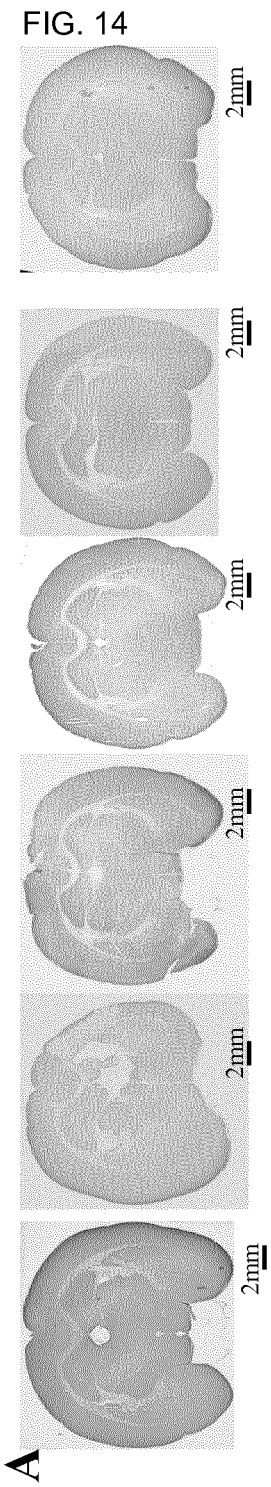
FIG. 14 Microtubule-associated protein 2 (MAP2) staining of brain coronal sections in rat pups treated with estetrol. At postnatal day 7, rat pups underwent hypoxic-ischemic insult. Upon retrieval from hypoxia, the rat pups were injected intraperitoneally by a single dose of (b) vehicle (Vehicle group, n=10), (c) 1 mg/kg E4 (n=10), (d) 5 mg/kg E4 (n=10), (e) 10 mg/kg E4 (n=10) or (f) 50 mg/kg E4 (n=10). Sham animals (a) underwent similar procedures without hypoxic-ischemic insult and were not injected with vehicle nor E4 (Sham group, n=10). Brains were removed upon sacrifice at postnatal day 14 and paraformaldehyde-fixed and paraffin-embedded brain samples were coronally sectioned at the hippocampus region. The sections were processed for detection of neuronal cytoskeletal disruption through immunohistological staining with anti-MAP2 antibody. (A) MAP2 staining of brain coronal sections (scale bar: 2 mm) is shown. (B) The ratio of the MAP2 positive areas was calculated as the MAP2 positive area of the ipsilateral hemisphere divided by the MAP2-positive area of the contralateral hemisphere. 10 samples from each group were analyzed. The ratio of the MAP2 positive area in the Sham group was considered by default as 1.0.
Figure 14:
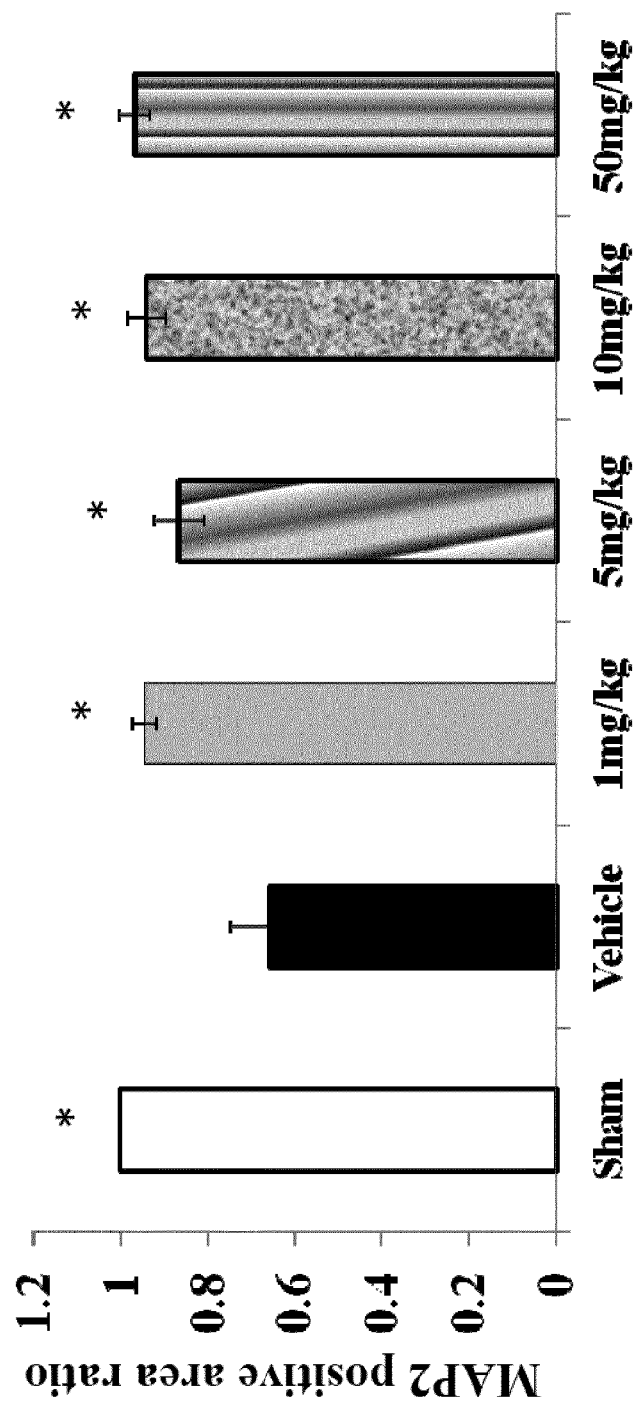

MAP2 Staining:

The same pattern of MAP2 staining was observed as in example 3. Quantification of the ratio of the MAP2-positive areas (FIG. 14B) revealed that the ratio of MAP2-positive area was significantly higher in sham operated animals (by default 1.0) (FIG. 14A(a)), and estetrol treated groups (1 mg/kg E4 (0.943±0.028) (FIG. 14A(c)), 5 mg/kg E4 0.89±0.037 (FIG. 143A(d)), 10 mg/kg E4 (0.938±0.044) (FIG. 14A(e)), 50 mg/kg E4 (0.966±0.036) (FIG. 14A(f))) than in the vehicle group (0.656±0.091) (FIG. 14A(b)).

Figure 15:
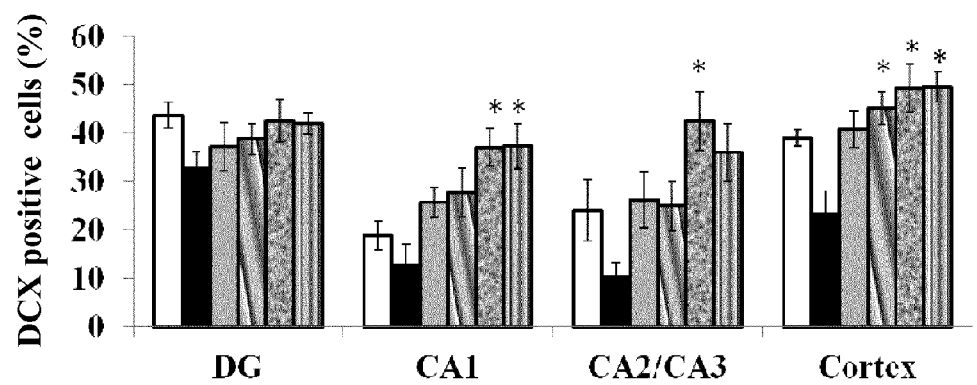
FIG. 15 Doublecortine (DCX) and Vascular Endothelial Growth Factor (VEGF) staining in hippocampus and cortex of rat pups treated with estetrol. At postnatal day 7, rat pups underwent hypoxic-ischemic insult. Upon retrieval from hypoxia, the rat pups were injected intraperitoneally by a single dose of vehicle (Vehicle group, n=10), 1 mg/kg E4 (n=10), 5 mg/kg E4 (n=10), 10 mg/kg E4 (n=10) or 50 mg/kg E4 (n=10). Sham animals (a) underwent similar procedures without hypoxic-ischemic insult and were not injected with vehicle nor E4 (Sham group, n=10). Brains were removed upon sacrifice at postnatal day 14 and paraformaldehyde-fixed and paraffin-embedded brain samples were coronally sectioned at the hippocampus region. The sections were double-stained with anti-DCX antibody and anti-VEGF antibody. The percentage of DCX (A) and VEGF (B) positive cells was quantified as the sum of either DCX or VEGF positively stained cells divided by the total number of DAPI positive cells. Quantifications were made in different regions of the hippocampus ((dentate gyrus (DG), cornu ammonis1 (CA1), cornu ammonis 2/3 (CA2/CA3)), and in the cortex. 10 samples were analyzed from each study group. For each indicated brain region (DG, CA1, CA2/3, Cortex on X-axis), the 6 bars represent, from left to right, percentage of DCX (A) or VEGF (B) positive cells in, respectively, Sham group, Vehicle group, 1 mg/kg E4 group, 5 mg/kg E4 group, 10 mg/kg E4 group, or 50 mg/kg E4 group. All measurements are shown as mean±SEM.
Figure 15:
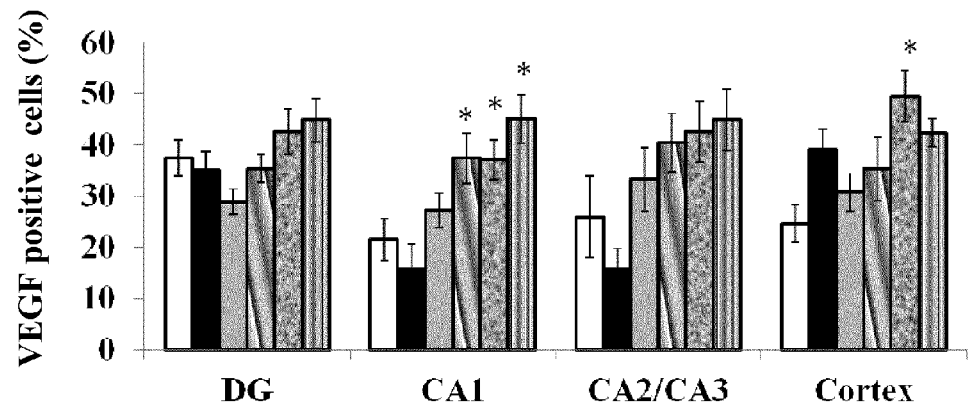

Doublecortine-Vascular Endothelial Growth Factor Double-Staining:

In the DG region of the hippocampus neither DCX nor VEGF staining was significantly different among the study groups (FIG. 15). In the CA1 region, the percentage of DCX positively stained cells was significantly higher in the 10 mg/kg E4 group (37.1±3.84) and 50 mg/kg E4 groups (37.3±4.784%) than in the vehicle group (12.8±2.947%) (FIG. 15 A), whereas the percentage of VEGF positively stained cells was significantly higher in the 5 mg/kg E4 group (37.4±4.833%), the 10 mg/kg E4 group (37.1±3.84%), and the 50 mg/kg E4 group (45.1±4.753%) than in vehicle treated animals (15.7±4.924%) (FIG. 15B). In the CA2/CA3 region the percentage of DCX positively stained cells was significantly higher in the 10 mg/kg E4 group (42.5±5.986%) than in vehicle treated animals (10.4±2.868%) (FIG. 15A), whereas the percentage of VEGF positively stained cells was not significantly different between the study groups (FIG. 15B). In the cortex the percentage of DCX positively stained cells was significantly higher in the 5 mg/kg E4 group (45.2±3.339%), the 10 mg/kg E4 group (49.4±4.949%), and the 50 mg/kg E4 group (49.6±3.11%) than in the vehicle group (23.3±4.74%) (FIG. 15A), whereas the percentage of VEGF positively stained cells was significantly lower in sham operated animals (24.6±3.7%) than in the 10 mg/kg E4 treated group (49.4±4.949%) (FIG. 15B).

Figure 16:
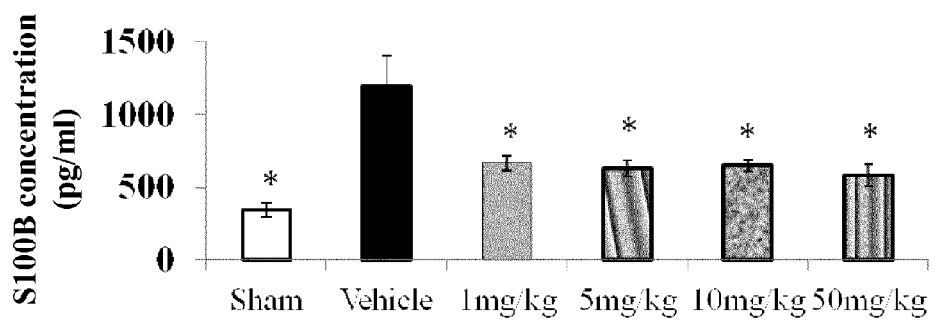
FIG. 16 S100B and Glial Fibrillary Acidic Protein (GFAP) expression in blood serum of rat pups that were treated with estetrol. At postnatal day 7, rat pups underwent hypoxic-ischemic insult. Upon retrieval from hypoxia, the rat pups were injected intraperitoneally by a single dose of vehicle (Vehicle group, n=14 and n=16 for S100B and GFAP, respectively)), 1 mg/kg E4 (n=13 and n=15 for S100B and GFAP, respectively), 5 mg/kg E4 (n=16 and n=15 for S100B and GFAP, respectively), 10 mg/kg E4 (n=13 and n=13 for S100B and GFAP, respectively) or 50 mg/kg E4 (n=15 and n=14 for S100B and GFAP, respectively). Sham animals (a) underwent similar procedures without hypoxic-ischemic insult and were not injected with vehicle nor E4 (Sham group, n=20 and n=21 for S100B and GFAP, respectively). Blood samples were drawn upon sacrifice at postnatal day 14. ELISA for S100B and GFAP proteins were performed to examine the concentration of S100B (A) GFAP (B) in the blood sera. All measurements are shown as mean±SEM.
Figure 16:
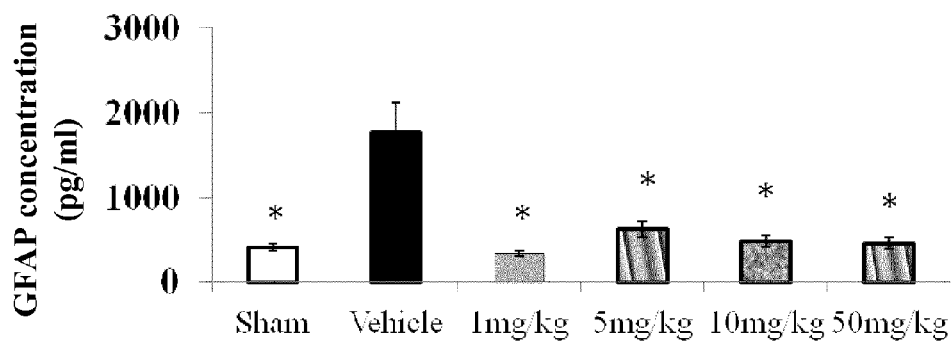

Blood serum S1008 and Glial Fibrillary Acidic Protein (GFAP):

As shown in FIG. 16, significantly lower expression of S100B and GFAP proteins is observed in sham operated animals and estetrol treated animals than in animals from the vehicle group.

Conclusion:

The present results demonstrate that estetrol has a therapeutic dose-dependent effect in the hippocampal formation and cortex in an animal model of HIE. Also in accordance to the present results, estetrol treatment decreases early gray matter loss and promotes neuro- and vasculogenesis. Moreover, estetrol treatment has no adverse effects on body weight, brain weight or body temperature.

Example 5

Therapeutic Effect of Estetrol in Newborns Following Perinatal or Neonatal Asphyxia Newborns who have suffered birth asphyxia and who exhibit at least one of the following symptoms: decreased consciousness and acidosis (pH<7.00 or base deficit≥12), 10-minute Apgar score≤5, or ongoing resuscitation at 10 minutes, are treated with estetrol.

Estetrol is administered intravenously as a single injection or by infusion within 6 hours after birth at a dose of 5 mg/kg body weight or 10 mg/kg body weight. Doses may be repeated.

Optionally, the newborns may simultaneously undergo hypothermia for 72 hours starting within 6 hours of delivery.

The invention claimed is:

1. A method of treatment of hypoxic-ischemic encephalopathy (HIE) in a subject in need thereof, comprising administering to the subject an amount of 1,3,5(10)-estratrien-3,15a,16a,17β-tetrol effective for said treatment.

2. The method of claim 1, wherein the treatment of the HIE is therapeutic.

3. The method according to claim 1, wherein the HIE is neonatal HIE.

4. The method according to claim 1 wherein the 1,3,5(10)-estratrien-3,15a,16a,17β-tetrol is administered within 12 hours after said HIE.

5. The method according to claim 4, wherein the 1,3,5(10)-estratrien-3,15a,16a,17β-tetrol is administered within 6 hours after said HIE.

6. The method of claim 3, wherein the 1,3,5(10)-estratrien-3,15a,16a,17β-tetrol is administered in combination with reducing body temperature to 33° C. to 34° C.

7. The method according to claim 1, wherein the 1,3,5(10)-estratrien-3,15a,16a,17β-tetrol is administered in a range from about 1 μg/kg to about 250 mg/kg body weight per day.

8. The method according to claim 7, wherein the 1,3,5(10)-estratrien-3,15a,16a,17β-tetrol is administered in doses of from about 0.05 mg/kg to about 100 mg/kg body weight for a period of a plurality of days until desired suppression of symptoms occurs.

9. The method of claim 8, wherein the doses are administered as a single daily dose, divided over one or more daily doses, or every week or longer.

10. The method of claim 7, wherein the 1,3,5(10)-estratrien-3,15a,16a,17β-tetrol is administered essentially continuously.

* * * * *